United States Patent
Saelens et al.

(10) Patent No.: US 10,023,629 B2
(45) Date of Patent: Jul. 17, 2018

(54) ANTI-INFLUENZA ANTIBODY

(71) Applicants: VIB VZW, Ghent (BE); Universiteit Gent, Ghent (BE); Vrije Universiteit Brussel, Brussels (BE)

(72) Inventors: Xavier Saelens, Ypres (BE); Francisco Miguel Lopez Cardoso, Ghent (BE); Ann DePicker, Schelderode (BE); Serge Muyldermans, Hoeilaart (BE)

(73) Assignees: VIB VZW (BE); UNIVERSITEIT GENT (BE); VRIJE UNIVERSITEIT BRUSSEL (BE)

( * ) Notice: Subject to any disclaimer, the term of this patent is extended or adjusted under 35 U.S.C. 154(b) by 266 days.

(21) Appl. No.: 14/651,043

(22) PCT Filed: Dec. 11, 2013

(86) PCT No.: PCT/EP2013/076200
§ 371 (c)(1),
(2) Date: Jun. 10, 2015

(87) PCT Pub. No.: WO2014/090865
PCT Pub. Date: Jun. 19, 2014

(65) Prior Publication Data
US 2016/0376347 A1    Dec. 29, 2016

(30) Foreign Application Priority Data
Dec. 11, 2012  (EP) .................................... 12196499

(51) Int. Cl.
*A61K 39/145* (2006.01)
*C07K 16/10* (2006.01)
*A61K 39/00* (2006.01)

(52) U.S. Cl.
CPC ........ *C07K 16/1018* (2013.01); *A61K 39/145* (2013.01); *A61K 2039/505* (2013.01); *C07K 2317/13* (2013.01); *C07K 2317/35* (2013.01); *C07K 2317/569* (2013.01); *C07K 2317/626* (2013.01); *C07K 2317/76* (2013.01)

(58) Field of Classification Search
None
See application file for complete search history.

(56) References Cited

U.S. PATENT DOCUMENTS

2012/0301394 A1* 11/2012 Movahedi ........ A61K 47/48484
424/1.49

FOREIGN PATENT DOCUMENTS

WO    2007/052242 A1    5/2007

OTHER PUBLICATIONS

Yondon et al. Equine Influenza A (H3N8) Virus isolated from Bactrian Camel, Mongolia, 2014, Emerging Infectious Diseases, vol. 20, No. 12, pp. 2144-2147.*
Aymard et al. (1999) "Role for Antibody to Neuraminidase in Protecting Against Influenza," Semaine Des Hopitaux De Paris. 75(23-24):933-941.—English Abstract Only.
Hultberg et al. (Apr. 2011) "Llama-derived single domain antibodies to build multivalent, superpotent and broadened neutralizing anti-viral molecules," PLoS One. 6(4):e17665.
Ibanez et al. (Apr. 2011) "Nanobodies with in vitro neutralizing activity protect mice against H5N1 influenza virus infection," J. Infect. Dis. 203(8):1063-1072.
Muyldermans (2001) "Single Domain Camel Antibodies: Current Status," Reviews in Molecular Biotechnology. 74:277-302.
Shoji et al. (Jan. 2011) "An influenza N1 neuraminidase-specific monoclonal antibody with broad neuraminidase inhibition activity against H5N1 HPAI viruses," Human Vaccines. 7 Suppl:199-204.
Vanlandschoot et al. (Sep. 2011) "Nanobodies: New ammunition to battle viruses," Antiviral Research. 92:389-407.
International Search Report corresponding to International Patent Application No. PCT/EP2013/076200, dated Feb. 18, 2014.

* cited by examiner

*Primary Examiner* — Benjamin P Blumel
(74) *Attorney, Agent, or Firm* — Lathrop Gage LLP; James H. Velema, Esq.

(57) ABSTRACT

The present invention relates to an antibody that confers protection against influenza virus infection. More specifically, it relates to an anti-neuraminidase antibody, protecting against highly pathogenic H5N1 influenza strains. The invention relates further to the use of the antibody for prophylactic and/or therapeutic treatment of influenza virus infections, and to a pharmaceutical composition comprising the antibody.

18 Claims, 12 Drawing Sheets

A.

B.

C.

B

C

A

B

C

D

E

F

G

SEQUENCE LISTING

```
<160> NUMBER OF SEQ ID NOS: 34

<210> SEQ ID NO 1
<211> LENGTH: 10
<212> TYPE: PRT
<213> ORGANISM: Artificial Sequence
<220> FEATURE:
<223> OTHER INFORMATION: nanobody

<400> SEQUENCE: 1

Gly Ser Ile Phe Ser Ile His Asp Met Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Nanobody

<400> SEQUENCE: 2
```

```
Gly Ser Asp Ile Ser Ile Tyr Glu Met Gly
1               5                   10

<210> SEQ ID NO 3
<211> LENGTH: 16
<212> TYPE: PRT
<213> ORGANISM: Artificial Sequence
<220> FEATURE:
<223> OTHER INFORMATION: nanobody

<400> SEQUENCE: 3

Ala Ile Thr Ser Gly Gly Ser Thr Asn Tyr Ala Asp Ser Val Lys Gly
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: nanobody

<400> SEQUENCE: 4

Ala Ile Thr Ser Gly Gly Thr Thr Asn Tyr Ala Asp Ser Val Lys Gly
1               5                   10                  15

<210> SEQ ID NO 5
<211> LENGTH: 12
<212> TYPE: PRT
<213> ORGANISM: Artificial Sequence
<220> FEATURE:
<223> OTHER INFORMATION: nanobody

<400> SEQUENCE: 5

Trp Gly Glu Asp Tyr Gly Leu Gly Glu Tyr Asp Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: nanobody

<400> SEQUENCE: 6

Ala Asp Phe Asp Leu Trp Glu Tyr Asp Tyr
1               5                   10

<210> SEQ ID NO 7
<211> LENGTH: 353
<212> TYPE: PRT
<213> ORGANISM: Artificial Sequence
<220> FEATURE:
<223> OTHER INFORMATION: Construct N1-3-VHH-Fc

<400> SEQUENCE: 7

Leu Gln Glu Ser Gly Gly Gly Leu Val Gln Pro Gly Gly Ser Leu Arg
1               5                   10                  15

Leu Ser Cys Ala Ala Ser Gly Ser Ile Phe Ser Ile His Asp Met Gly
                20                  25                  30

Trp Tyr Arg Arg Arg Pro Gly Lys Gln Arg Glu Leu Val Ala Ala Ile
                35                  40                  45

Thr Ser Gly Gly Ser Thr Asn Tyr Ala Asp Ser Val Lys Gly Arg Phe
        50                  55                  60

Thr Ile Ser Arg Asp Asn Ala Lys Asn Thr Val Ser Leu Gln Met Asn
```

```
                65                  70                  75                  80
        Ser Leu Lys Pro Glu Asp Thr Ala Val Tyr Tyr Cys Asn Ala Trp Gly
                        85                  90                  95

Glu Asp Tyr Gly Leu Gly Glu Tyr Asp Ser Trp Gly Gln Gly Thr Gln
                        100                 105                 110

Val Thr Val Ser Ser Pro Arg Gly Pro Thr Ile Lys Pro Cys Pro Pro
                        115                 120                 125

Cys Lys Cys Pro Ala Pro Asn Leu Leu Gly Gly Pro Ser Val Phe Ile
                        130                 135                 140

Phe Pro Pro Lys Ile Lys Asp Val Leu Met Ile Ser Leu Ser Pro Ile
        145                 150                 155                 160

Val Thr Cys Val Val Val Asp Val Ser Glu Asp Asp Pro Asp Val Gln
                        165                 170                 175

Ile Ser Trp Phe Val Asn Asn Val Glu Val His Thr Ala Gln Thr Gln
                        180                 185                 190

Thr His Arg Glu Asp Tyr Asn Ser Thr Leu Arg Val Val Ser Ala Leu
                        195                 200                 205

Pro Ile Gln His Gln Asp Trp Met Ser Gly Lys Glu Phe Lys Cys Lys
                        210                 215                 220

Val Asn Asn Lys Asp Leu Pro Ala Pro Ile Glu Arg Thr Ile Ser Lys
        225                 230                 235                 240

Pro Lys Gly Ser Val Arg Ala Pro Gln Val Tyr Val Leu Pro Pro Pro
                        245                 250                 255

Glu Glu Glu Met Thr Lys Lys Gln Val Thr Leu Thr Cys Met Val Thr
                        260                 265                 270

Asp Phe Met Pro Glu Asp Ile Tyr Val Glu Trp Thr Asn Asn Gly Lys
                        275                 280                 285

Thr Glu Leu Asn Tyr Lys Asn Thr Glu Pro Val Leu Asp Ser Asp Gly
                        290                 295                 300

Ser Tyr Phe Met Tyr Ser Lys Leu Arg Val Glu Lys Lys Asn Trp Val
        305                 310                 315                 320

Glu Arg Asn Ser Tyr Ser Cys Ser Val Val His Glu Gly Leu His Asn
                        325                 330                 335

His His Thr Thr Lys Ser Phe Ser Arg Thr Pro Gly Lys Lys Asp Glu
                        340                 345                 350

Leu

<210> SEQ ID NO 8
<211> LENGTH: 351
<212> TYPE: PRT
<213> ORGANISM: Artificial Sequence
<220> FEATURE:
<223> OTHER INFORMATION: Construct N1-5-VHH-Fc

<400> SEQUENCE: 8

Leu Gln Glu Ser Gly Gly Gly Leu Val Gln Pro Gly Gly Ser Leu Arg
1               5                   10                  15

Leu Ser Cys Ala Ala Ser Gly Ser Asp Ile Ser Ile Tyr Glu Met Gly
                20                  25                  30

Trp Tyr Arg Gln Ala Pro Gly Lys Gln Arg Glu Leu Val Ala Ala Ile
                35                  40                  45

Thr Ser Gly Gly Thr Thr Asn Tyr Ala Asp Ser Val Lys Gly Arg Phe
                50                  55                  60

Thr Ile Ser Arg Asp Asn Ala Lys Asn Thr Val Tyr Leu Gln Met Asn
65                  70                  75                  80
```

```
Ser Leu Lys Pro Glu Asp Thr Ala Val Tyr Tyr Cys Asn Ala Ala Asp
                85                  90                  95

Phe Asp Leu Trp Glu Tyr Asp Tyr Trp Gly Gln Gly Thr Gln Val Thr
            100                 105                 110

Val Ser Ser Pro Arg Gly Pro Thr Ile Lys Pro Cys Pro Pro Cys Lys
        115                 120                 125

Cys Pro Ala Pro Asn Leu Leu Gly Gly Pro Ser Val Phe Ile Phe Pro
130                 135                 140

Pro Lys Ile Lys Asp Val Leu Met Ile Ser Leu Ser Pro Ile Val Thr
145                 150                 155                 160

Cys Val Val Val Asp Val Ser Glu Asp Pro Asp Val Gln Ile Ser
                165                 170                 175

Trp Phe Val Asn Asn Val Glu Val His Thr Ala Gln Thr Gln Thr His
            180                 185                 190

Arg Glu Asp Tyr Asn Ser Thr Leu Arg Val Val Ser Ala Leu Pro Ile
        195                 200                 205

Gln His Gln Asp Trp Met Ser Gly Lys Glu Phe Lys Cys Lys Val Asn
210                 215                 220

Asn Lys Asp Leu Pro Ala Pro Ile Glu Arg Thr Ile Ser Lys Pro Lys
225                 230                 235                 240

Gly Ser Val Arg Ala Pro Gln Val Tyr Val Leu Pro Pro Glu Glu
                245                 250                 255

Glu Met Thr Lys Lys Gln Val Thr Leu Thr Cys Met Val Thr Asp Phe
            260                 265                 270

Met Pro Glu Asp Ile Tyr Val Glu Trp Thr Asn Asn Gly Lys Thr Glu
        275                 280                 285

Leu Asn Tyr Lys Asn Thr Glu Pro Val Leu Asp Ser Asp Gly Ser Tyr
290                 295                 300

Phe Met Tyr Ser Lys Leu Arg Val Glu Lys Lys Asn Trp Val Glu Arg
305                 310                 315                 320

Asn Ser Tyr Ser Cys Ser Val Val His Glu Gly Leu His Asn His His
                325                 330                 335

Thr Thr Lys Ser Phe Ser Arg Thr Pro Gly Lys Lys Asp Glu Leu
            340                 345                 350

<210> SEQ ID NO 9
<211> LENGTH: 263
<212> TYPE: PRT
<213> ORGANISM: Artificial Sequence
<220> FEATURE:
<223> OTHER INFORMATION: Construct N1-3-VHHb

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile His
                20                  25                  30

Asp Met Gly Trp Tyr Arg Arg Ala Pro Gly Lys Gln Arg Glu Leu Val
            35                  40                  45

Ala Ala Ile Thr Ser Gly Gly Ser Thr Asn Tyr Ala Asp Ser Val Lys
        50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Asn
                85                  90                  95
```

```
Ala Trp Gly Glu Asp Tyr Gly Leu Gly Glu Tyr Asp Ser Trp Gly Gln
            100                 105                 110

Gly Thr Gln Val Thr Val Ser Ala His His Ser Glu Asp Pro Ser
            115                 120                 125

Ser Lys Ala Pro Lys Ala Pro Met Ala Gln Val Gln Leu Gln Glu Ser
            130                 135                 140

Gly Gly Gly Leu Val Gln Pro Gly Gly Ser Leu Arg Leu Ser Cys Ala
145                 150                 155                 160

Ala Ser Gly Ser Ile Phe Ser Ile His Asp Met Gly Trp Tyr Arg Arg
                165                 170                 175

Ala Pro Gly Lys Gln Arg Glu Leu Val Ala Ala Ile Thr Ser Gly Gly
            180                 185                 190

Ser Thr Asn Tyr Ala Asp Ser Val Lys Gly Arg Phe Thr Ile Ser Arg
            195                 200                 205

Asp Asn Ala Lys Asn Thr Val Ser Leu Gln Met Asn Ser Leu Lys Pro
            210                 215                 220

Glu Asp Thr Ala Val Tyr Tyr Cys Asn Ala Trp Gly Glu Asp Tyr Gly
225                 230                 235                 240

Leu Gly Glu Tyr Asp Ser Trp Gly Gln Gly Thr Gln Val Thr Val Ser
                245                 250                 255

Ser His His His His His His
            260

<210> SEQ ID NO 10
<211> LENGTH: 252
<212> TYPE: PRT
<213> ORGANISM: Artificial Sequence
<220> FEATURE:
<223> OTHER INFORMATION: Construct N1-5-VHHb

<400> SEQUENCE: 10

Leu Gln Glu Ser Gly Gly Gly Leu Val Gln Pro Gly Gly Ser Leu Arg
1               5                   10                  15

Leu Ser Cys Ala Ala Ser Gly Ser Asp Ile Ser Ile Tyr Glu Met Gly
                20                  25                  30

Trp Tyr Arg Gln Ala Pro Gly Lys Gln Arg Glu Leu Val Ala Ala Ile
            35                  40                  45

Thr Ser Gly Gly Thr Thr Asn Tyr Ala Asp Ser Val Lys Gly Arg Phe
        50                  55                  60

Thr Ile Ser Arg Asp Asn Ala Lys Asn Thr Val Tyr Leu Gln Met Asn
65                  70                  75                  80

Ser Leu Lys Pro Glu Asp Thr Ala Val Tyr Tyr Cys Asn Ala Ala Asp
                85                  90                  95

Phe Asp Leu Trp Glu Tyr Asp Tyr Trp Gly Gln Gly Thr Gln Val Thr
            100                 105                 110

Val Ser Ser Ala His His Ser Glu Asp Pro Ser Ser Lys Ala Pro Lys
        115                 120                 125

Ala Pro Met Ala Leu Gln Glu Ser Gly Gly Gly Leu Val Gln Pro Gly
    130                 135                 140

Gly Ser Leu Arg Leu Ser Cys Ala Ala Ser Gly Ser Asp Ile Ser Ile
145                 150                 155                 160

Tyr Glu Met Gly Trp Tyr Arg Gln Ala Pro Gly Lys Gln Arg Glu Leu
                165                 170                 175

Val Ala Ala Ile Thr Ser Gly Gly Thr Thr Asn Tyr Ala Asp Ser Val
            180                 185                 190
```

```
Lys Gly Arg Phe Thr Ile Ser Arg Asp Asn Ala Lys Asn Thr Val Tyr
        195                 200                 205

Leu Gln Met Asn Ser Leu Lys Pro Glu Asp Thr Ala Val Tyr Tyr Cys
    210                 215                 220

Asn Ala Ala Asp Phe Asp Leu Trp Glu Tyr Asp Tyr Trp Gly Gln Gly
225                 230                 235                 240

Thr Gln Val Thr Val Ser Ser His His His His His
            245                 250

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
gtcctggctg ctcttctaca agg                                        23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggtacgtgct gttgaactgt tcc                                        23

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
gatgtgcagc tgcaggagtc tggrggagg                                  29

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
ggactagtgc ggccgctgga gacggtgacc tgggt                           35

<210> SEQ ID NO 15
<211> LENGTH: 29
<212> TYPE: DNA
<213> ORGANISM: Artificial Sequence
<220> FEATURE:
<223> OTHER INFORMATION: primer

<400> SEQUENCE: 15
gatgtgcagc tgcaggagtc tggrggagg                                  29

<210> SEQ ID NO 16
<211> LENGTH: 35
<212> TYPE: DNA
<213> ORGANISM: Artificial Sequence
<220> FEATURE:
```

<223> OTHER INFORMATION: Primer

<400> SEQUENCE: 16
ggactagtgc ggccgctgga gacggtgacc tgggt                              35

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
tcacacagga aacagctatg ac                                            22

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
cgccagggtt ttcccagtca cgac                                          24

<210> SEQ ID NO 19
<211> LENGTH: 75
<212> TYPE: DNA
<213> ORGANISM: Artificial Sequence
<220> FEATURE:
<223> OTHER INFORMATION: primer

<400> SEQUENCE: 19
catgccatgg gagctttggg agctttggag ctgggggtct tcgctgtggt gcgctgagga   60
gacggtgacc tgggt                                                    75

<210> SEQ ID NO 20
<211> LENGTH: 55
<212> TYPE: DNA
<213> ORGANISM: Artificial Sequence
<220> FEATURE:
<223> OTHER INFORMATION: primer

<400> SEQUENCE: 20
catgccatga tccgcggccc agccggccat ggctgatgtg cagctggtgg agtct        55

<210> SEQ ID NO 21
<211> LENGTH: 122
<212> TYPE: PRT
<213> ORGANISM: Artificial Sequence
<220> FEATURE:
<223> OTHER INFORMATION: NB1 (Figure 2A)

<400> SEQUENCE: 21

Gln Val Gln Leu Gln Glu Ser Gly Gly Gly Leu Val Gln Ala Gly Gly
1               5                   10                  15

Ser Leu Arg Leu Ser Cys Thr Ala Ser Gly Gly Thr Phe Ser Ser Tyr
            20                  25                  30

Pro Met Gly Trp Phe Arg Gln Ala Pro Gly Lys Glu Arg Glu Phe Val
        35                  40                  45

Ala Ala Ile Ser Trp Ser Gly Gly Ser Thr Asn Tyr Ala Asp Ser Val
    50                  55                  60

Lys Gly Arg Phe Thr Ile Ser Arg Asp Asn Ala Lys Thr Thr Val Tyr

```
            65                  70                  75                  80
Leu Gln Met Asn Ser Leu Lys Pro Glu Asp Thr Ala Val Tyr Tyr Cys
                85                  90                  95

Asn Ala Glu Gly Asp Ser Asp Ser Pro Ala Leu Gly Met Asp Tyr Trp
            100                 105                 110

Gly Lys Gly Thr Gln Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: NB2 (Figure 2A)

<400> SEQUENCE: 22

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Leu Ser Thr Tyr Tyr Ala Asp Ser Val
    50                  55                  60

Lys Gly Arg Phe Ser Ile Ser Arg Asp Asn Ala Lys Asn Met Val Tyr
65                  70                  75                  80

Leu Gln Met Asn Ser Leu Lys Pro Glu Asp Thr Ala Val Tyr Tyr Cys
                85                  90                  95

Asn Ala Asp Pro Arg Ala Arg Thr Thr Gly Trp Ala Pro Ser Gly Asp
            100                 105                 110

Trp Gly Gln Gly Thr Gln Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: NB3 (Figure 2A)

<400> SEQUENCE: 23

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile His
            20                  25                  30

Asp Met Gly Trp Tyr Arg Arg Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Asn
                85                  90                  95

Ala Trp Gly Glu Asp Tyr Gly Leu Gly Glu Tyr Asp Ser Trp Gly Gln
            100                 105                 110

Gly Thr Gln Val Thr Val Ser Ser
        115                 120
```

<210> SEQ ID NO 24
<211> LENGTH: 121
<212> TYPE: PRT
<213> ORGANISM: Artificial Sequence
<220> FEATURE:
<223> OTHER INFORMATION: NB4 (Figure 2A)

<400> SEQUENCE: 24

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Phe Ser Leu Tyr
            20                  25                  30

Ser Met Ala Trp Tyr Arg Gln Ala Pro Gly Lys Gln Arg Glu Leu Val
        35                  40                  45

Ala Asp Ile Thr Ser Gly Gly Ala Thr Asn Tyr Ala Asp Ser Val Lys
    50                  55                  60

Gly Arg Phe Thr Ile Ser Arg Val Asn Ala Lys Asn Thr Val Tyr Leu
65                  70                  75                  80

His Met Asn Asn Leu Lys Pro Glu Asp Thr Ala Val Tyr Tyr Cys Asn
                85                  90                  95

Ala Asp Ala Ser Ser Asp Tyr Gly Leu Ser Phe Phe Asp Ser Trp Gly
            100                 105                 110

Gln Gly Thr Gln Val Thr Val Ser Ser
        115                 120
```

<210> SEQ ID NO 25
<211> LENGTH: 118
<212> TYPE: PRT
<213> ORGANISM: Artificial Sequence
<220> FEATURE:
<223> OTHER INFORMATION: NB5 (Figure 2A)

<400> SEQUENCE: 25

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Asp Ile Ser Ile Tyr
            20                  25                  30

Glu Met Gly Trp Tyr Arg Gln Ala Pro Gly Lys Gln Arg Glu Leu Val
        35                  40                  45

Ala Ala Ile Thr Ser Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Ala Asp Phe Asp Leu Trp Glu Tyr Asp Tyr Trp Gly Gln Gly Thr
            100                 105                 110

Gln Val Thr Val Ser Ser
        115
```

<210> SEQ ID NO 26
<211> LENGTH: 120
<212> TYPE: PRT
<213> ORGANISM: Artificial Sequence
<220> FEATURE:
<223> OTHER INFORMATION: NB6 (Figure 2A)

<400> SEQUENCE: 26

```
Gln Val Gln Leu Gln Glu Ser Gly Gly Gly Leu Val Gln Pro Gly Gly
```

-continued

```
                1               5                   10                  15
Ser Leu Arg Leu Ser Cys Ala Ala Ser Gly Ile Ile Phe Ser Ile Tyr
                    20                  25                  30

Val Met Gly Trp Tyr Arg Gln Ala Pro Gly Lys Gln Arg Glu Leu Val
            35                  40                  45

Ala Ala Ile Thr Glu Gly Gly Ser Thr Asn Tyr Ala Asp Ser Val Lys
        50                  55                  60

Gly Arg Phe Thr Ile Ser Arg Asp Asn Ala Met Asn Thr Val Tyr Leu
65                  70                  75                  80

Gln Met Asn Ser Leu Lys Pro Glu Asp Thr Ala Val Tyr Tyr Cys Asn
                85                  90                  95

Ala Ile Thr Pro Asp Gly Ser Leu Trp Glu Ala Asp Tyr Trp Gly Gln
            100                 105                 110

Gly Thr Gln Val Thr Val Ser Ser
            115                 120
```

<210> SEQ ID NO 27
<211> LENGTH: 124
<212> TYPE: PRT
<213> ORGANISM: Artificial Sequence
<220> FEATURE:
<223> OTHER INFORMATION: NB7 (Figure 2A)

<400> SEQUENCE: 27

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Arg Phe Ser Arg Tyr
                    20                  25                  30

Asp Met Gly Trp Tyr Arg Gln Ala Pro Gly Lys Gln Arg Glu Leu Val
            35                  40                  45

Ala Thr Ile Thr Ser Gly Gly Ile Thr Asn Tyr Ala Asp Ser Val Lys
        50                  55                  60

Gly Arg Phe Thr Ile Ser Arg Asp Asn Thr Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Asp Pro Leu Arg Ala Ile Gln Leu Gly Ser Leu Thr Tyr Glu
            100                 105                 110

Tyr Trp Gly Gln Gly Thr Gln Val Thr Val Ser Ser
            115                 120
```

<210> SEQ ID NO 28
<211> LENGTH: 124
<212> TYPE: PRT
<213> ORGANISM: Artificial Sequence
<220> FEATURE:
<223> OTHER INFORMATION: NB8 (Figure 2A)

<400> SEQUENCE: 28

```
Gln Val Gln Leu Gln Glu Ser Gly Gly Gly Met Val Gln Pro Gly Gly
1               5                   10                  15

Ser Leu Arg Val Ser Cys Ala Ala Ser Gly Ser Arg Phe Ser Arg Tyr
                    20                  25                  30

Asp Met Gly Trp Tyr Arg Gln Ala Pro Gly Lys Gln Arg Glu Leu Val
            35                  40                  45

Ala Thr Ile Thr Ser Gly Gly Ile Thr Asn Tyr Ala Asp Ser Val Lys
        50                  55                  60
```

Gly Arg Phe Thr Ile Ser Arg Asp Asn Thr Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Asp Pro Leu Arg Ala Ile Gln Leu Gly Ser Leu Thr Tyr Glu
            100                 105                 110

Tyr Trp Gly Gln Gly Thr Gln Val Thr Val Ser Ser
            115                 120

<210> SEQ ID NO 29
<211> LENGTH: 114
<212> TYPE: PRT
<213> ORGANISM: Artificial Sequence
<220> FEATURE:
<223> OTHER INFORMATION: NB9 (Figure 2A)

<400> SEQUENCE: 29

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Lys Trp Tyr Arg Gln Ala Pro Gly Lys Glu Arg Glu Leu Val
        35                  40                  45

Ala Glu Ile Ser Ser Arg Gly Gly Thr Thr Asn Tyr Ala Asp Pro Val
    50                  55                  60

Lys Gly Arg Phe Thr Ile Ser Arg Asp Asn Phe Lys Asn Met Val Tyr
65                  70                  75                  80

Leu Gln Met Asn Ser Leu Lys Pro Glu Asp Thr Ala Val Tyr Tyr Cys
                85                  90                  95

Asn Arg Pro His Pro Asp Tyr Trp Gly Arg Gly Thr Gln Val Thr Val
            100                 105                 110

Ser Ser

<210> SEQ ID NO 30
<211> LENGTH: 114
<212> TYPE: PRT
<213> ORGANISM: Artificial Sequence
<220> FEATURE:
<223> OTHER INFORMATION: NB10 (Figure 2A)

<400> SEQUENCE: 30

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Lys Trp Tyr Arg Gln Ala Pro Gly Lys Glu Arg Glu Leu Val
        35                  40                  45

Ala Glu Ile Ser Ser Arg Gly Gly Thr Thr Asn Tyr Ala Asp Pro Val
    50                  55                  60

Lys Gly Arg Phe Thr Ile Ser Arg Asp Asn Phe Lys Asn Met Val Tyr
65                  70                  75                  80

Leu Gln Met Asn Ser Leu Lys Pro Glu Asp Thr Ala Val Tyr Tyr Cys
                85                  90                  95

Asn Arg Pro His Pro Asp Tyr Trp Gly Gln Gly Thr Gln Val Thr Val
            100                 105                 110

Ser Ser

```
<210> SEQ ID NO 31
<211> LENGTH: 114
<212> TYPE: PRT
<213> ORGANISM: Artificial Sequence
<220> FEATURE:
<223> OTHER INFORMATION: NB11 (Figure 2A)

<400> SEQUENCE: 31

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Lys Trp Tyr Arg Gln Ala Pro Gly Lys Glu Arg Glu Leu Val
        35                  40                  45

Ala Glu Ile Ser Ser Arg Gly Gly Thr Thr Asn Tyr Ala Asp Ser Val
    50                  55                  60

Lys Gly Arg Phe Thr Ile Ser Arg Asp Asn Phe Arg Asn Met Val Tyr
65                  70                  75                  80

Leu Gln Met Asn Ser Leu Lys Pro Glu Asp Thr Ala Val Tyr Tyr Cys
                85                  90                  95

Asn Arg Pro His Pro Asp Tyr Trp Gly Gln Gly Thr Gln Val Thr Val
            100                 105                 110

Ser Ser

<210> SEQ ID NO 32
<211> LENGTH: 114
<212> TYPE: PRT
<213> ORGANISM: Artificial Sequence
<220> FEATURE:
<223> OTHER INFORMATION: NB12 (Figure 2A)

<400> SEQUENCE: 32

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Lys Trp Tyr Arg Gln Ala Pro Gly Lys Glu Arg Glu Leu Val
        35                  40                  45

Ala Glu Ile Ser Ser Arg Gly Gly Thr Thr Asn Tyr Ala Asp Ser Val
    50                  55                  60

Lys Gly Arg Phe Thr Ile Ser Arg Asp Asn Ile Lys Asn Met Val Tyr
65                  70                  75                  80

Leu Gln Met Asn Ser Leu Lys Pro Glu Asp Thr Ala Val Tyr Tyr Cys
                85                  90                  95

Asn Arg Pro His Pro Asp Tyr Trp Gly Gln Gly Thr Gln Val Thr Val
            100                 105                 110

Ser Ser

<210> SEQ ID NO 33
<211> LENGTH: 118
<212> TYPE: PRT
<213> ORGANISM: Artificial Sequence
<220> FEATURE:
<223> OTHER INFORMATION: NB13 (Figure 2A)

<400> SEQUENCE: 33

Gln Val Gln Leu Gln Glu Ser Gly Gly Gly Met Val Gln Pro Gly Gly
1               5                   10                  15

Ser Leu Arg Leu Thr Cys Ala Ala Ser Gly Phe Thr Phe Ser Ser Tyr
```

```
                        20                  25                  30
Asp Met Ser Trp Val Arg Gln Ala Pro Gly Lys Gly Pro Glu Arg Val
        35                  40                  45

Ser Ala Ile Asp Ile Gly Gly Gly Ser Thr Tyr Tyr Ala Asn Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Val Arg Asp Trp Tyr Gly Leu Ala Arg Arg Tyr Arg Gly Gln Gly Thr
                100                 105                 110

Gln Val Thr Val Ser Ser
                115

<210> SEQ ID NO 34
<211> LENGTH: 4
<212> TYPE: PRT
<213> ORGANISM: Artificial Sequence
<220> FEATURE:
<223> OTHER INFORMATION: ER retention signal

<400> SEQUENCE: 34

Lys Asp Glu Leu
1
```

ANTI-INFLUENZA ANTIBODY

RELATED APPLICATIONS

This application is a 35 U.S.C. § 371 filing of International Application No. PCT/EP2013/076200, filed Dec. 11, 2013, which claims priority to European Patent Application No. 12196499.3, filed Dec. 11, 2012, each of which is incorporated herein by reference in its entirety.

The present invention relates to an antibody that confers protection against influenza. More specifically, it relates to an anti-neuraminidase antibody, protecting against highly pathogenic H5N1 influenza strains. The invention relates further to the use of the antibody for prophylactic and/or therapeutic treatment of influenza virus infections, and to a pharmaceutical composition comprising the antibody.

The zoonotic influenza infections in humans present a persistent and great burden worldwide to health, academic and pharmaceutical entities. The possibility of a highly pathogenic influenza pandemic in humans had been recognized, which, if present, not only can present a high toll to human society, but could also change the importance and perceived danger of infectious diseases in the social and cultural context. In less than 10 years, two zoonotic outbreaks had a major global impact: the Avian Influenza Virus (AIV) (Tran et al., 2004) and the swine flu (H1N1) or "Mexican flu", confirmed the lack of preparedness against a highly pathogenic pandemic (Ilyushina et al., 2010). Among these zoonotic influenza outbreaks, the avian H5N1 influenza virus is one of the most concerning because of the vast animal reservoir for this virus (domesticated as well as wild water fowl) and the high lethality rate in humans. Indeed, infection of humans with highly pathogenic H5N1 (HPAI H5N1) influenza virus results in a 60% mortality rate (Chotpitayasunondh et al., 2005). This high pathogenicity and lethality of the HPAIV H5N1 in humans can be attributed to a high replication rate and a broad cellular tropism that can lead to a systemic spread. During severe infections, a deregulated induction of proinflammatory cytokines and chemokines (sometimes called "cytokine storm") is associated with HPAI H5N1 infections, that can result into an excessive immunological response and autoimmune symptoms (de Jong et al., 2006).

The treatments reported and available against HPAI H5N1 are far from optimal. The currently licensed influenza antiviral drugs remain the most used treatment HPAI H5N1, even though they were developed against seasonal human influenza viruses. These drugs target only two viral proteins: the proton ion channel M2 (amantadine and rimantadine) and the sialidase Neuraminidase (oseltamivir, zanamivir and peramivir). The efficacy of these drugs depends greatly of the severity of the H5N1 infection, that itself depends on several factors like: patient age, activity, previous vaccination and previous exposure to similar Influenza strains. In addition, the use of influenza antiviral drugs for hospitalized patients is often characterized by long term treatment and high concentrations are used in severe clinical cases. Such treatment regimes represent a major concern because they favor selective pressure causing the appearance of reported and emerging drug-resistant mutants. Moreover, bacterial secondary infections are associated with influenza and complicate the clinical outcome (Hebert et al., 1992; Rameix-Welti et al., 2009). On the other hand, the vaccination strategy used against seasonal influenza is not efficient in preventing or controlling zoonotic or pandemic Influenza virus treatment, due to the unpredictability in their occurrence, the antigenic mismatch between such vaccines and pandemic viruses and the lack of immunological memory in human. The recent reports of experimental adaptation of H5N1 virus for airborne transmission in ferrets, confirm the possibility of human to human transmission of zoonotic HPAI H5N (Herfst et al., 2012; Imai et al., 2012). Treatment of patients with convalescent plasma from influenza HPAI H5N1 (Zhou et al., 2007) and H1N1 (Hung et al., 2011) survivors patients has been shown to be protective. However, those data are based on a limited number of patients, treatment with convalescent plasma is certainly not generally accepted as a therapy and there are practical limitations in collecting convalescent plasma (Wong et al., 2010).

Influenza NA best known function is to prevent aggregation of the newly produced virions by cleaving the sialic acids from the infected cell and from the viral glycoproteins. In addition, other functions had been reported for the NA, pointing out its relevance in several parts of the replicative cycle of Influenza (Air et al., Influenza Other Respi Viruses. 2012 Jul. 6(4): 245-56). The immunogenicity of the influenza virion depends mainly of the two major proteins in its surface, the Hemagglutinin (HA) and the NA. It has been reported that the HA is immunodominant over the NA with respect to T- and B-cell priming (Johansson et al., 1987), but their disassociation re-established an equal immunogenic potential of both viral proteins (Johansson and Kilbourne 1993). A high immunogenic potential of the NA had been reported, and it has been proposed to depend in some degree of defective ribosomal products (DRiP) by presenting NA peptides to the MHC class I molecules for T cell activation, enabling rapid immunosurveillance (Dolan et al., 2010). Nowadays, the evidence of the importance in the immune response dependent of NA, leads to the proposal of standardize the NA content in the seasonal vaccine formulation (Johansson et al., 1998) (Kilbourne et al., 2004). In addition, the pace with which HA and NA drift in human influenza A viruses is similar, suggesting the selection pressure of the human host directed against the two glycoproteins of influenza viruses is comparable (Westgeest et al., JGV, 2012, September; 93(Pt 9): 1996-2007).

Besides the immunogenicity of NA and its receptor destroying activity that avoids virion aggregation, there are another NA roles reported: cleavage of decoy receptors in the mucins, which is necessary during the initiation of infection (Matrosovich et al., 2004); limitation of Influenza superinfections and possible reassortment (Huang et al., 2008); possibility of increased infectivity (Goto and Kawaoka 1998). Interestingly, Influenza virus sensitive to NA inhibitory drugs resulted in a crippled or absence of NA activity (Ilyushina et al., 2012). These data confirms that the fitness of these mutant virus can be rescued by decreased HA binding to Neu5Ac receptors, which had been reported due to insertions of mutations or glycosylations that affect the receptor binding site (Gubareva et al., 2002). Such compensatory effect in the HA and NA activities towards fitness had been widely reported (Gubareva et al., 2002; Mitnaul et al., 2000; Nedyalkova et al., 2002), demonstrating that the NA activity can be compromised, but not necessarily results in a replication deficient virus. These pieces of evidence highlight the complexity of the mechanism of Influenza escape mutants under selective pressure. There also important roles of the NA function that do not depend of the catalytic site: enhancement of neurovirulence (e.g. the glycan at position 130, (Li et al., 1993); enhanced pathogenicity (length of NA stalk; Matsuoka et al., 2009; Yamada et al., 2006). Taken together, these data demonstrate the major importance of the NA in influenza A virus infection, indicating that targeting NA may result in a global effective antiviral strategy, dependent or independent of the NA catalytic activity.

Several authors have disclosed methods for passive immunization using monoclonal antibodies. WO2009035420 discloses monoclonal antibodies against H5N1 hemagglutinin and neuraminidase, and the use of the hemagglutinin antibodies in treatment of influenza infection. However, whereas protection using the hemagglutinin antibodies is demonstrated, no evidence for protection using the neuraminidase antibodies is shown. Shoji et al. (2011) and WO2010037046 describe a humanized neuraminidase antibody, its production in plants and the use of this antibody for treatment of influenza virus infection. However, a high amount of antibody is needed and even then, the survival after challenge is only 50% in their animal model. There is still need for antibodies that can be effectively used in passive immunization, resulting in a high protection and survival after lethal challenge.

Surprisingly we found that high affinity VHHs can be generated targeting the Influenza NA. The high affinity of these monomeric VHH to a recombinant N1 (recN1) results also in highly potent H5N1 inhibitors in vitro. The introduction of bivalent formats in the VHH increased the antiviral potential in vitro and rescued H5N1 lethality challenged mice. Even more surprisingly, bivalent VHHs, either by fusion of the VHH to an Fc tail or by linking the VHHs to an IgG2c hinge resulted in an unexpected increase in potency of the nanobodies, giving full protection against a lethal challenge in a mouse model, while using low amounts of antibodies.

A first aspect of the invention is a variable domain of camelid heavy chain antibodies (VHH) specifically binding influenza neuraminidase. Preferably, said neuraminidase is an influenza type N1 neuraminidase. Preferably, said VHH is inhibiting the neuraminidase activity. Even more preferably, said VHH comprises a CDR1 loop sequence selected from the group consisting of SEQ ID No 1 and SEQ ID No 2, a CDR2 loop sequence selected from the group consisting of SEQ ID No 3 and SEQ ID No 4 and a CDR3 loop sequence consisting of SEQ ID No 5 and SEQ ID No 6.

Another aspect of the invention is an influenza neuraminidase binding construct, comprising a VHH according to the invention. Preferably, said neuraminidase is a type N1 neuraminidase. Said influenza binding construct may be any VHH binding construct; preferably it is a fusion protein, even more preferably it is a bivalent or multivalent construct, comprising more than one influenza neuraminidase binding VHHs. In one preferred embodiment, the VHH according to the invention is fused to an Fc tail. In another preferred embodiment, two VHHs are linked by an IgG2c hinge. Preferably, the construct according to the inventions comprises a sequence, even more preferably consist of a sequence selected from the group consisting of SEQ ID No 7, SEQ ID No 8, SEQ ID No 9 and SEQ ID No 10.

Still another aspect of the invention is an influenza neuraminidase binding construct, according to the invention for use in treatment of influenza infections. Treatment, as used here, may be prophylactic and/or therapeutic treatment. Preferably, said influenza is selected from the group consisting of H5N1 and H1N1 influenza, more preferably said influenza is a H5N1 strain.

Still another aspect of the invention is a pharmaceutical composition, comprising an influenza binding neuraminidase construct according to the invention, preferably in combination with a suitable excipient. Said pharmaceutical composition may be any pharmaceutical composition known to the person skilled in the art, including, but not limited to compositions for systemic, oral and intranasal delivery.

EXAMPLES

Figure 1:
FIG. 1. Characterization and production of recombinant H5N1 NA. Soluble recombinant NA derived from A/crested eagle/Belgium/01/2004 was produced in SF9 cells using the Baculovirus expression platform. A. Diagram of the expression cassette in the pACMP2 vector: Promoter, Baculovirus basic protein promoter; ssHA, secretion signal of Hemagglutinin; tGCN4, tetramerizing leucine zipper; H5N1 NA, extracellular domain of the H5N1 NA. B. Sialidase activity in crude culture supernatant of infected SF9 cells. Supernatants of different amounts of Baculovirus N1rec infected cells and mock infected cells were measured in a MUNANA based NA activity test. C. Chromatographic elution profile of the fractions of N1rec after superdex 200 gel filtration. The highest NA activity was localized in the fractions F19-F26. D. Coomassie stained SDS-PAGE and immunoblot against N1rec, of F19-F26 from D: 18 μl and 9 μl of eluted fractions from the gel filtration were loaded on the SDS-PAGE and immunoblot, respectively.
Figure 1:
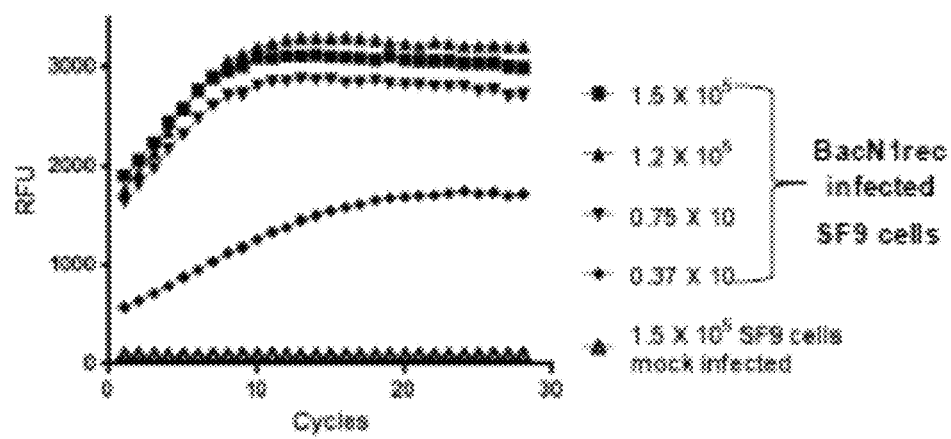
Figure 1:
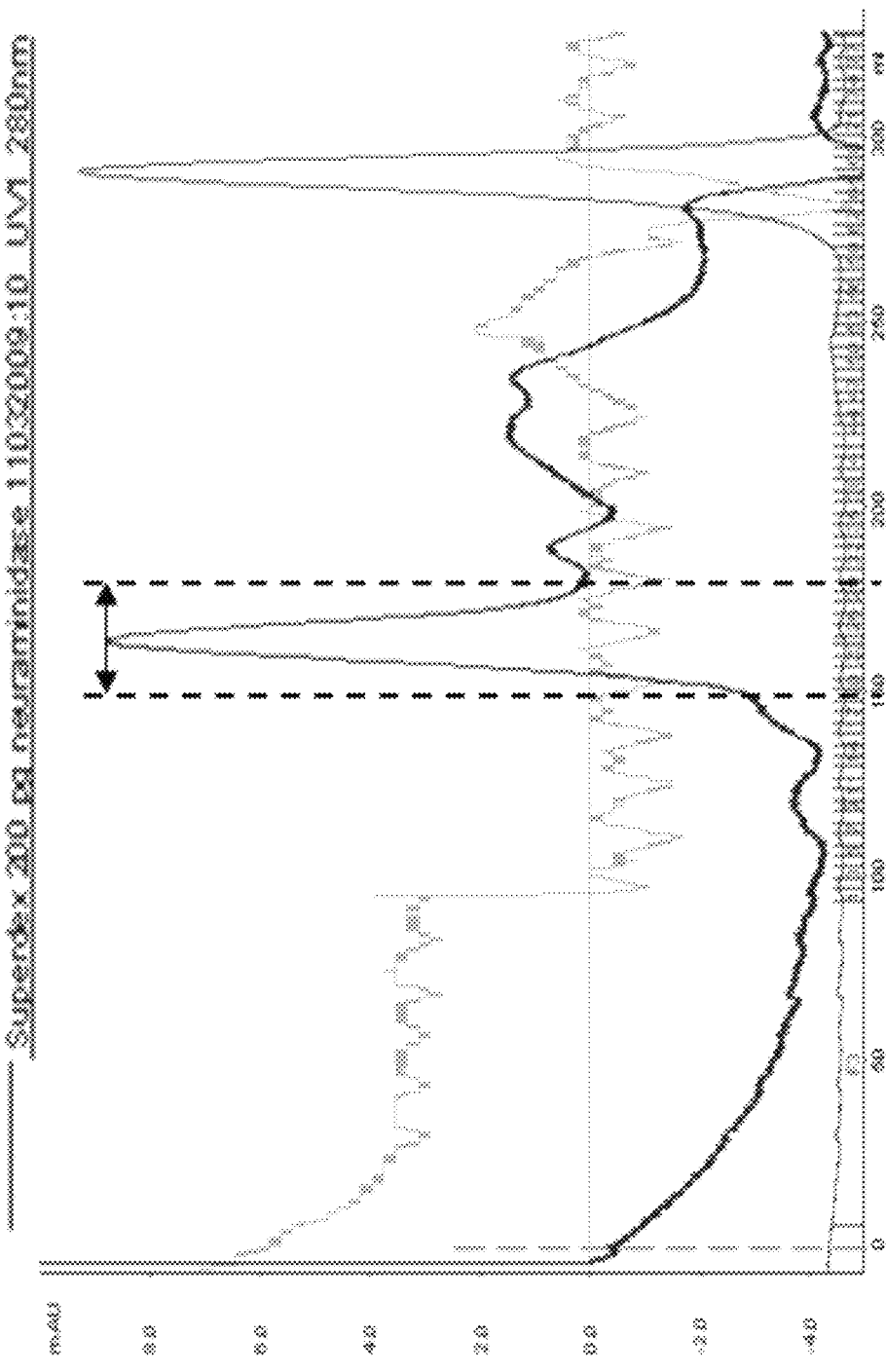
Figure 1:
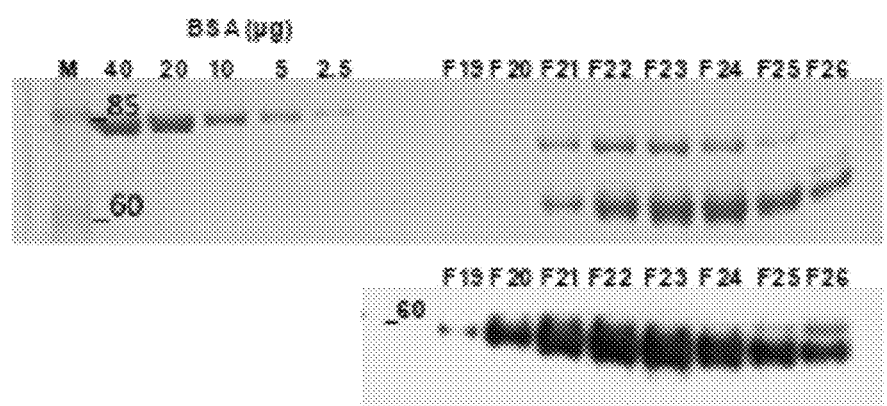

Materials and Methods to the Examples
Influenza Viruses

H5N1 IAV strains NIBRG-14 and NIBRG-23 were obtained from the UK National Institute for Biological Standards and Control, a center of the Health Protection Agency. NIBRG-14 and NIBRG-23 are 2:6 reverse genetics-derived reassortants with NA and HA (lacking the polybasic cleavage site) segments derived from A/Vietnam/1194/2004 (H5N1) and A\turkey\Turkey\2005 (H5N1), respectively, and the other six segments from A/PR/8/34 (H1N1) viruses. The H5N1 H274Y virus described here is a 1:1:6 reverse genetics-derived reassortant, with NA derived from A/crested eagle/Belgium/01/2004 (Van Borm et al., 2005) carrying the H274Y mutation introduced by site-specific mutagenesis, HA from NIBRG-14, and the remaining six genome segments from A/PR/8/34 (Hoffman et al., 2002). This virus was rescued by transfection of co-cultured HEK-293T and MDCK cells. The supernatant from these cells was used for end point dilution to obtain a clonal H5N1 H274Y virus sample that was subsequently amplified on MDCK cells, pelleted from the cell supernatant, and mouse adapted by serial passage in BALB/c mice. All HA segments of these H5N1 viruses lack the coding information for the polybasic cleavage site. Following adaptation to BALB/c mice, the HA and NA-coding regions of the mouse-adapted NIBRG-14 (NIBRG-14 ma) and H5N1 H274Y (H5N1 H274Y ma) were sequenced and found to be identical to those of the parental viruses. pH1N1 (kindly provided by Dr. Bernard Brochier, Scientific Institute of Public Health, Brussels, Belgium) is derived from a clinical isolate of the pH1N1 virus of 2009 and was adapted to mice by serial passages (Schotsaert et al, 2013). The median tissue culture infectious dose (TCID50) and median lethal dose (LD50) of NIBRG-14 ma and H5N1 H274Y ma viruses were calculated by the method of Reed and Muench (1938). All the H5N1 and pH1N1 experiments described above were performed in BSL-2+ rooms.

Baculovirus Production of the N1rec

The N1rec expression cassette gene (n1rec) consisted of: hemaglutinin type 1 signal sequence (ssHA, 16 residues), a tetramerizing leucine zipper derived from transcription factor GCN4 (tGCN4, 32 residues) (Harbury, Zhang et al. 1993), and the extracellular part of the H5N1 NA derived from A/crested eagle/Belgium/09/2004 (53-449 amino acid residues) (Van Borm, Thomas et al. 2005). This expression cassette was cloned into a pAcMP2 Baculovirus transfer vector (BD Biosciences®), resulting in the pAcMP2n1rec vector. The *Autografa californica* nuclear poliedrosis virus (AcNPV) derived BaculoGold Linearized Baculovirus DNA (BD Biosciences®), and the pACMp2n1rec were cotransfected in the clonal tissue culture line Sf9 derived from *Spodoptera frugiperda*, by the ESCORT IV Transfection Reagent (Sigma®), resulting in the recombinant AcNPVN1rec virus. The transfected SF9 cells were incubated at 28° C. in rolling tubes for 4 days. Then, $4 \times 10^8$ cells SF9 cells were infected with a multiplicity of infection (moi) of 10. After 7 days the supernatant was centrifuged 1 hr at 50000 g, and the NA activity was measured.

Neuraminidase Activity Assay.

NA activity was quantified by measuring the rate of cleavage of the fluorogenic substrate 4-MUNANA (2'-4-Methylumbelliferyl-α-D-N-acetylneuraminic acid, sodium salt hydrate (Sigma-Aldrich) into 4-methylumbelliferone. The NA activity reaction was performed in 200 mM NaAc, 2 mM CaCl2 with 1% butanol and 1 mM 4-MUNANA and measured in a kinetic mode, with excitation at 365 nm and emission at 450 nm in an Optima Fluorostar. A standard curve of increasing concentrations of soluble 4-methylumbelliferone was included to correlate the fluorescence intensity with the molar amount of 4-methylumbelliferone. One NA activity unit is defined as the activity needed to generate 1 nmol of 4-methylumbelliferone per min.

Fetuin (5 µg/ml; Sigma-Aldrich) was coated on Nunc 96 well plates overnight at 4° C. Excess fetuin was washed away with PBS, and IAV dilutions (diluted in PBS with 1 mM CaCl2 and 0.5 mM MgCl2), with or without added single domain antibodies, were added and incubated 1 h at 37° C. The amount of desialylated fetuin was measured by colorimetry to determine binding of horseradish peroxidase (HRP) coupled peanut agglutinin (PNA, Sigma-Aldrich). The plates were washed three times with PBS+0.1% Tween 20 and then incubated with 50 µl PNA-HRP (2.5 µg/ml in PBS+0.05% Tween 20) at room temperature. Then the plates were washed three times with PBS, after which 50 µl of TMB substrate (Pharmigen BD) was added and absorbance was measured at 450 nm with a reference at 650 nm. In the Accelerated Viral Inhibition Assay (AVINA) (Hassantoufighi et al., 2010), IAV dilutions containing the indicated N1-VHHm concentrations were transferred to a black 96-well plate and 75 µl of 20 µM MUNANA was added and incubated 1 h at 37° C. Then, 100 µl stop solution (0.1 M glycine, pH 10.7, 25% ethanol) was added to each well, and fluorescence was determined. For the AVINA and fetuin substrate assays, we used the following amounts of IAV: 7×105 pfu of NIBRG-14 ma, 1×104 pfu of H5N1 H274Y ma, and 3×104 plaque forming units (pfu) of pH1N1.

N1rec Purification

Two parts of n-butanol were added to 3 parts of cleared AcNPVN1rec infected SF9 cells supernatant. An aqueous phase, containing the soluble N1rec, was extracted from a lipid phase, and was 2.5 times diluted in 5 mM KH2PO4 pH 6.6 and 0.22 μm filtered. The diluted aqueous phase was applied to a HA Ultrogel® Hydroxyapatite Chromatography Sorbent (Pall®) packed XK26\70 column (GE Healthcare®), and eluted with a gradient of 5 mM KH2PO4 pH 6.6, 4% butanol to 400 mM KH2PO4 pH 6.6, 4% butanol. Eluted fractions that scored positive to NA activity were pooled and loaded into a 50 mM MES pH 6.6, 5% glycerol, 8 mM $CaCl_2$ equilibrated 10 ml column packed with Blue Sepharose (Sigma-Aldrich®). A single step elution was done with 50 mM MES pH 6.6, 5% glycerol, 8 mM $CaCl_2$, 1.5 NaCl. A desalting step was performed by gel filtration in XK70 packed with HiLoad 16/60 Superdex 200 pg (GE Healthcare®) column equilibrated with 50 mM MES pH 6.6, 5% glycerol, 8 mM $CaCl_2$, 150 mM NaCl. All the chromatography steps were performed on an Akta purification station (GE Healthcare®).

Camelid Immunization and Phage Library Construction

An alpaca (*Vicugna pacos*) was weekly injected subcutaneously with 125 μg of N1rec during 35 days. On day 39, anticoagulated blood was collected for the preparation of lymphocytes. Lymphocytes were isolated using a UNI-SEP density gradient separation kit (NOVAmed®), and total RNA was extracted. cDNA was prepared using using oligo (dT) primers, and the VH and VHH genes were amplified with: primer call 01 (GTCCTGGCTGCTCTTCTACAAGG) (SEQ ID No 11) and primer call 02 (GGTACGTGCTGTTGAACTGTTCC) (SEQ ID No 12). The PstI and NotI restriction sites were inserted into the amplified sequences using the primers: A6E (GAT GTG CAG CTG CAG GAG TCT GGR GGA GG) (SEQ ID No 13) and 38 (GGA CTA GTG CGG CCG CTG GAG ACG GTG ACC TGG GT) (SEQ ID No 14). The PCR 550 bp product and the vector pHEN4 were PstI and NotI digested and ligated (Arbabi Ghahroudi, Desmyter et al. 1997). This ligation was used for the transformation of electrocompetent TG1 *E. coli* cells, and was growth in 2×TY (100 μg/ml ampicilin and 1% glucose) into the exponential phase, and the helper phage M13K07 was added. The library was subjected to 4 consecutive rounds of panning, performed in solid-phase coated N1rec (200 μg/ml) to select N1rec-binding phages.

N1-VHHm Production and Purification.

The VHH genes of the selected N1rec binding phages, contained in the pHEN4 phagemid, were amplified by PCR amplification with the primers: A6E (GAT GTG CAG CTG CAG GAG TCT GGR GGA GG) (SEQ ID No 15) and 38 (GGA CTA GTG CGG CCG CTG GAG ACG GTG ACC TGG GT) (SEQ ID No 16). A 400 bp PCR product and the pHEN6c vector were PstI and BstEII digested and purified with the PCR product purification kit (Roche®) and ligated. Competent *E. coli* WK6 strains were transformed with the ligation mix. Positive colonies were screened by PCR amplification for a 550 bp fragment using the primers: universal reverse primer (TCACACAGGAAACAGCTATGAC) (SEQ ID No 17) and the universal forward primer (CGCCAGGGTTTTCCCAGTCACGAC) (SEQ ID No 18). The VHH gene cloned in the pHEN6c vector contains PelB signal sequence at the N-terminus and a hexahistidine tag at the C-terminus. WK6 cells transformed with the pHEN6c harboring the VHH genes were growth in TB medium supplemented with ampicilin (100 μg/ml), 2 mM $CaCl_2$ and 0.1% glucose. The production of the VHH was induced with 1 mM of IPTG, and periplasm was extracted by osmotic shock. The periplasmic extracts were obtained by osmotic shock using TES (0.2 M Tris pH 8.0, 0.5 mM EDTA and 0.5 M sucrose). Periplasmic extracts were centrifuged at 8000 rpm at 4° C. and the supernatant was applied to a His Select Nickel Affinity gel (Sigma®), washed with PBS and the soluble VHH was eluted with 0.5 Imidazole and dialyzed at 4° C. with PBS by ultrafiltration (cutoff 3.5 kDa). Concentration of the monomeric VHH (VHHm) was performed in a Vivaspin 5000 MW (Vivascience®). Total protein concentration was determined with BCA protein Assay kit (Thermo Scientific).

Theorical N1-VHHm Structure Prediction

The amino acid sequence of the 13 different candidates VHH directed against NA were loaded in the ESyPred3D Web Server 1.0 Molecular Biology Research Unit, The University of Namur, Belgium (www.unamur.be/sciences/biologie/urbm/bioinfo/esypred/) and retrieved as PDB files. The structure of the 13 N1-VHHm were modelled with PyMOL Molecular Graphics System (Delano Scientific).

VHH Surface Plasmon Resonance Analysis

The affinity of the N1-3-VHHm, N1-5-VHHm and N1-7-VHHm elicited against N1rec were determined by surface plasmon resonance (SPR) on a Biacore3000. N1rec antigen was first immobilized (2000 RU) into a Series S sensor chip CM5 (GE Healthcare®) (coupling was in 10 mM NaAc pH 4.5), with regeneration in 0.02% SDS. Subsequently, each N1-VHHm was diluted in HBS buffer (0.01 M HEPES, 0.15 M NaCl, 0.005% Tween 20, pH 6.4) to arrive at a concentration between 1.95 and 1000 nM and was injected over the CM5 chip to record its binding kinetics with the N1rec. Binding sensograms were used to calculate the $k_{on}$ and $k_{off}$ values with the Biacore T100 evaluation software and to determine the equilibrium dissociation constant ($K_D$) and the epitome analysis.

Construction of the N1-VHH Bivalent

The genes encoding the N1-3-VHHm or the N1-5-VHHm were amplified with primers MH (5'-CATGCCATGGGAGCTTTGGGAGCTTTGGAGCTGGGGGTCTTCGCTGTGGTGCGCTGAGGAGACGGTGACCTGGGT-3') (SEQ ID No 19) and A4short (5'-CATGCCATGATCCGCGGCCCAGCCGGCCATGGCTGATGTGCAGCTGGTGGAGTCT-3') (SEQ ID No 20) to introduce a NcoI restriction enzyme site at both extremities of the amplified fragment. The MH primer also added the hinge sequence of Ilama γ2c (AL-His-His-Ser-Glu-Asp-Pro-Ser-Ser-Lys-Ala-Pro-Lys-Ala-Pro-Met-Ala) (Hmila, Saerens et al. 2010) to the 3' end of the VHH. The PCR-amplified product was then purified with PCR product purification kit (Roche®). The PCR product and the pHEN6c plasmid containing the n1-3-vhh or the n1-5-vhh genes were digested for several hours with NcoI enzyme and treated with alkaline phosphatase, and then purified. Finally, the pHEN6 recombinant plasmid and the PCR fragment were ligated with T4 DNA ligase (Fermentas®). The ligated product was used to transform *E. coli* WK6 electrocompetent cells. Clones were screened by PCR using the universal forward and reverse sequencing primers for the presence of the bivalent construct. The amplification products of ca 1000 bp were sequenced to ensure the absence of unintended mutations. After expression, the encoded protein was tested for binding to N1rec by ELISA. To obtain larger amounts of the tandemly linked bispecific N1-VHH construct, the protocols for the expression and purification conditions of the N1-VHHm were followed (see above).

Plant Produced N1-VHH-Fc Expression Cassette The n1-vhh-fc expression cassette was designed as follows, from 5' to 3': LB (left border of T-DNA); 3' ocs (3' end of the octopine synthase gene); npt II (neomycin phosphotransferase II open reading frame); Pnos (nophaline synthase gene promoter); Pphas (β-phaseolin gene promoter); 5' utr (5' UTR of arc5-I gene); SS (signal peptide of the *Arabidopsis thaliana* 2S2 seed storage protein gene); KDEL (ER retention signal) (SEQ ID No 34); n1-3-vhh (coding sequence of the N1-3-VHH); 3' arc (3' flanking regulatory sequences of the arc5-I gene); n1-3-vhh (coding sequence of the N1-3-VHH fused to the mouse CH2 and CH3 IgG2a hinge sequence); RB, T-DNA right border (De Jaeger, Scheffer et al. 2002) (Van Droogenbroeck, Cao et al. 2007). This expression cassette was synthesized in the commercial vector pUC57 (GenScript®), and cloned into a pPhasGW binary T-DNA vector, resulting in the pPhasGWn1-vhh-fc vector.

Production and Purification of Soluble N1-VHH-Fc

The pPhasGWn1-vhh-fc was used for transformation of *Agrobacterium* C58C1Rif$^R$(pMP90). This *Agrobacterium* strain was grown on YEB medium supplemented with rifampicin (100 mg/L), gentamycin (40 mg/L), spectinomycin (100 mg/L) and streptomycin (300 mg/L). *Arabidopsis* transformants are obtained via *Agrobacterium*-mediated floral dip transformation (Clough and Bent 1998). Seeds from T1 segregating plants were crushed and total protein was extracted with: 50 mM Tris-HCl, pH 8.0, 200 mM NaCl, 5 mM EDTA, 0.1% (v/v) of Tween 20 and Complete® protease inhibitor tablets (Roche®). The seed extracts were applied to a protein G sepharose column (GE Healthcare®) and eluted fractions were analysed.

Inhibitory Immune Plaque Assay

Monolayers of MDCK cells were grown in DMEM supplemented with 10% Fetal Bovine Serum, 1% penicillin/streptomycin, 1% glutamine at 37° C. with 5% $CO_2$. MDCK TMPRRS2 medium was supplemented with geneticin (0.3 mg/ml) and puromycin (2 µg/ml) and the expression of TMPRSS2 was induced with doxycyclin (0.5 µg/ml). At 70% of confluency, the MCDK cells were infected with a moi of 10 with the corresponding virus. The antiviral treatment was mixed with 0.8% of Avicel RC-591 as an overlay (Matrosovich, Matrosovich et al. 2006). After different times of incubation, cells were fixed with 4% paraformalfehyde in PBS for 30 min. The cells were permeabilized with 20 mM glycine, 0.5% (v/v) Triton X-100. After blocking, the cells were incubated for 2 hrs with polyclonal α-NIBRG-14 (1:1000) and α-M2e (Mab 148, 1:5000). After washing, α mouse IgG-HRP conjugated was used to visualize plaques using the substrate TrueBlue™ Peroxidase Substrate (KPL®).

Neuraminidase Sequences Alignment

The phylogentic tree and aminoacids substitutions of the aligned sequences of the H5N1 NA of: A/crested eagle/Belgium/01/2004 (accession number: ABP52007), A/Vietnam/1194/2004 (ABA70757) and A/turkey/Turkey/01/2005 (ABQ58915), were obtained by the Clustal W method, in the MegAlign software (DNASTAR®).

Prophylactic Efficacy Studies in Mice

Specific-pathogen-free female BALB/c mice, 7-9 weeks old, were purchased from Charles River (Germany) and used for all experiments. Mice were housed in cages individually ventilated with high-efficiency particulate air filters in temperature-controlled, air-conditioned facilities with food and water ad libitum. Mice were anesthetized by intraperitoneal injection of xylazine (10 µg/g) and ketamine (100 µg/g) before intranasal administration of N1-VHH or challenge virus (50 µL, divided equally between the nostrils). The N1-VHH in any format were diluted in endotoxin-free phosphate-buffered saline (PBS) with 1% (wt/vol) bovine serum albumin and administered as a single dose, ranging from 100 to 0.5 µg per mouse (5-0.25 mg/kg). To determine the effect of intranasal N1-VHH delivery on lung virus titer production, mice were challenged with 4 $LD_{50}$ of NIBRG-14ma virus. Lung homogenates were prepared in PBS, cleared by centrifugation at 4° C., and used for virus titration. Monolayers of MDCK cells were infected with 50 µL of serial 1:10 dilutions of the lung homogenates, in a 96-well plate in serum-free Dulbecco's modified Eagle medium (Invitrogen) supplemented with penicillin and streptomycin. After 1 h, the inoculum was replaced by medium containing 2 µg/ml of L-(tosylamido-2-phenyl) ethyl chloromethyl ketone-treated trypsin (Sigma). Endpoint virus titers were determined by hemagglutination of chicken red blood cells and expressed as $TCID_{50}$ per milliliter. Influenza RNA levels were determined with quantitative polymerase chain reaction (PCR). RNA was isolated from 150 µL of cleared lung homogenate using the Nucleospin RNA virus kit (Machery-Nagel®). The relative amount of NIBRG-14ma genomic RNA was determined by preparing viral cDNA and performing quantitative PCR with M-genomic segment primers 5'tcgaaaggaacagcagagtg3' and 5'ccagctctatgctgacaaaatg3' and probe 5'ggatgctg3' (probe no. 89; Universal ProbeLibrary, Roche) and the LightCycler 480 Real-Time PCR System (Roche). To determine the degree of protection against mortality, mice were challenged with 4 $LD_{50}$ of NIBRG-14ma virus and subsequently monitored for 14 days. A 30% loss in body weight drop was the end point at which moribund mice were euthanized. All animal procedures were approved by the Institutional Ethics Committee on Experimental Animals.

Statistical Analysis

Graphpad (Graphpad Prism®, version 5) was used for statistical analysis. Differences between groups were tested using the 2-way ANOVA. When this test demonstrated a significant difference between groups (P<0.05), t tests were used to compare 2 groups. Kaplan-Meier survival curves were plotted and evaluated.

Example 1: Production of Recombinant Tetrameric Neuraminidase

A Baculovirus Expression Vector System (BEVS) was used to produce a recombinant H5N1 NA derived from A/crested eagle/Belgium/09/2004. The N1rec expression cassette gene (n1rec) (FIG. 1A) was cloned into a pAcMP2 expression vector (pAcMP2n1rec), under the control of the AcNPV basic protein promoter, an infectious cycle late phase promoter preferred for the production of proteins with post-translational modifications (BD Biosciences®). Infection of *Spodoptera frugiperda* (SF9) cells with a recombinant baculovirus containing the N1rec expression cassette resulted in sialidase activity in the cell supernatant suggesting that the N1rec product was soluble and enzymatically active tetrameric NA (FIG. 1B). The N1rec in the culture supernatant was purified from the culture supernatant (Table 1). Following a final size exclusion chromatography step, we obtained 90% pure N1rec (FIG. 1C). The theoretical molecular weight of N1rec is 49.5 kDa. The relative electrophoretic mobility in SDS-PAGE suggested a size of approximately 60 kDa (FIG. 1D), presumably due to the presence of glycosylations; there are predicted 3 N-glycosylation and 2 O-glycosylation sites in the N1rec. The purified protein had a specific activity of 25058.89. NA units/mg of total protein (Table 1).

TABLE 1

Progressive enrichment of eluted fractions of N1 NA through the purification process

|  | Volume (ml) | Total NA units\ mg total protein [a] | Relative purity |
|---|---|---|---|
| Infected Sf9 supernatant | 1650 | 20605.92 | n.d [b] |
| Aqueous phase | 1450 | 13115.45 | n.d |
| Hydroxyapatite Elution | 555 | 12080.01 | 35% |
| Blue sepharose Elution | 15 | 56850.90 | 80% |
| Superdex 200 Elution | 11 | 21801.24 | 90% |

[a] Based in a NA inhibition assay using the substrate 2'-(4-methylumbelliferyl)-a-D-N acetylneuraminic acid (MUNANA), expressed in NA units (1 unit neuraminidase = nmoles 4-methylumbelliferone/min).
[b] Not determined.

Example 2: Immunization and VHH Phage Library Construction

Figure 2:
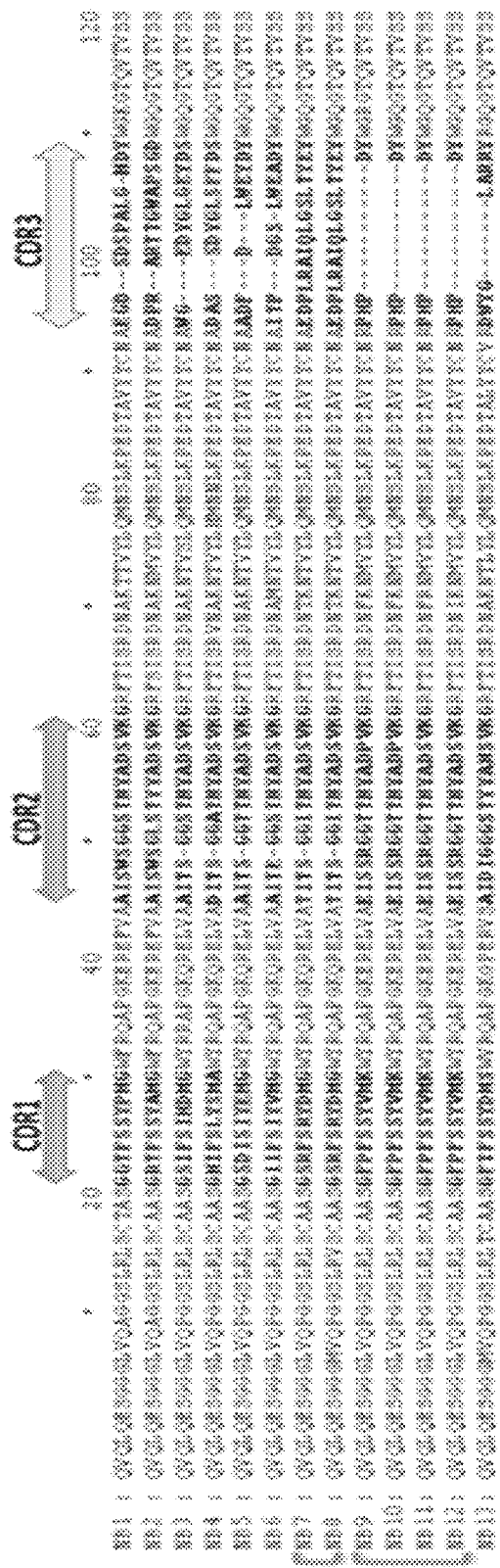
FIG. 2. Characterization of the H5N1 NA-binding VHHs. A. Alignment of the VHH amino acid sequence of the 13 VHHs (SEQ ID No 21-33) that were isolated by phage-display generated from a N1-rec immunized Alpaca. The four framework regions are separated by 3 Complementary Determining Regions (CDRs, left-right arrows). The VHH CDR3 (yellow arrow) is the most variable region in the VHH candidates. The blue brackets on the left indicate VHHs from the same clonal family, depicted by * and ° symbols. B. In silico predicted 3D-structure of the VHHs, showing electropositive (blue) and electronegative (red) potential. The white ribbon represents the CDR3. Note that N1-1-VHH, N1-3-VHH, N1-4-VHH, N1-5-VHH and N1-6-VHH CDR3 present an electronegative protruding topology. C. Coomassie-blue stained reducing SDS-PAGE of the purified *E. coli*-produced N1-VHHm candidates. Twenty μg of SA-VHHm was loaded as control VHH. The VHH size ranges from 14-15 kDa. Purified BSA standards were loaded for quantification and comparison.
Figure 2:
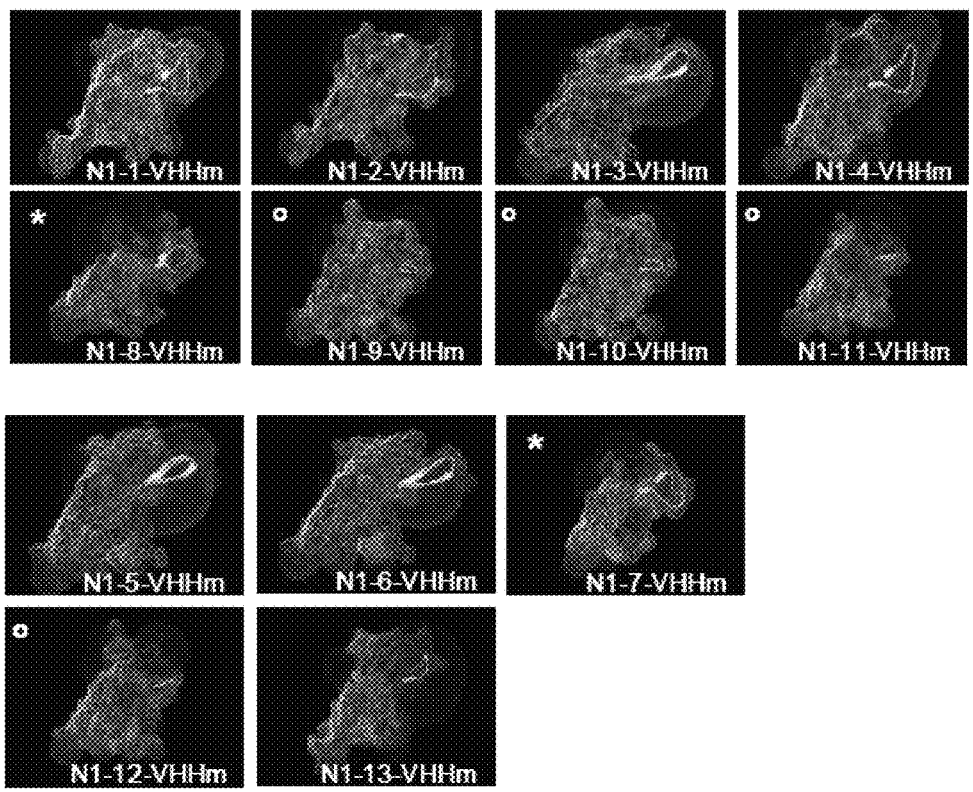
Figure 2:
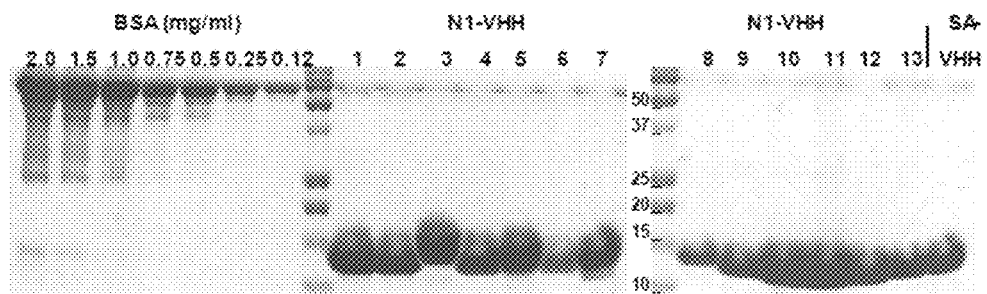

N1rec was next used as an immunogen for the generation and selection of NA-specific VHH. An alpaca (*Vicunia pacos*) was immunized at day 0 with 125 μg of N1rec, followed by 6 weekly boosts. One week after the last immunization, blood was collected and peripheral blood lymphocytes were isolated. From the lymphocytes, total RNA was extracted and used as template for cDNA synthesis. The VH and VHH genes were amplified by PCR, and the VHH genes were isolated and cloned into the phagemid vector pHEN4 (Arbabi Ghahroudi, Desmyter et al. 1997). We obtained a VHH phage library of $2 \times 10^8$ independent transformants. Fifty seven % of these transformants harboured a pHEN4 with a VHH cDNA insert of the correct size (550 bp). The VHH phage display library was then subjected to four consecutive rounds of panning, performed on solid-phase coated N1rec antigen. From the panning, 78 positive clones were retained. Subsequent Restriction fragment Length Polyphormism analysis narrowed down the N1rec-specific VHH candidates to 24 colonies, encoding 13 different VHHs. Sequences analysis of these 13 VHHs allowed classifying them into 9 clonally related groups, with differences mainly in the CDR3 domain sequence (FIG. 2A). We named these N1rec-binding VHHs N1-(1-13)-VHH. The in silico predicted topology of the 13 N1-VHH, suggested that they covered a diverse range of CDR3 structures (FIG. 2B). Some of the N1-VHH structures showed a protruding electronegatively charged CDR3 (e.g. N1-3-VHHm, FIG. 2B).

Example 3: Production and Characterization of Soluble N1-VHHm

The coding information for each of the 13 N1-VHH candidates was transferred into the bacterial expression vector pHEN6 under the control of a lac operon, for expression and purifications purposes (Kang, Jones et al. 1991). The transformation of amber suppressor *E. coli* strain WK6 with the pHEN6n1-vhh produced a monomeric N1-VHH (N1-VHHm) that is targeted to the periplasm and C-terminally tagged with hexahistidine. Following osmotic shock, periplasmic extracts were prepared and loaded onto a nickel sepharose column, to purify a set of 13 N1-VHH proteins (FIG. 2C). The binding of each of the 13 N1-VHHm to the NA part of N1rec, but not to the tGCN4 moiety, was confirmed by ELISA (data not shown). We next assessed the capacity of our monovalent N1-VHHm candidates to inhibit the enzymatic activity of N1rec. For this, we used a small substrate-based fluorogenic assay to evaluate the potential inhibitory activity of our N1-VHHm. Interestingly, 4 candidates; N1-1-VHHm, N1-3-VHHm, N1-5-VHHm and N1-6-VHHm could inhibit the N1rec catalytic activity (Table 2). The N1-3-VHHm and the N1-5-VHHm were the most potent inhibitors of the N1rec catalytic activity (Table 3), and together with N1-7-VHHm, were analysed by surface plasmon resonance using immobilized N1rec. The N1-7-VHHm was included in this analysis as a binding but non-inhibitory N1-VHHm control. Both N1-3-VHHm and N1-5-VHHm presented a high affinity for N1rec, with an equilibrium dissociation constant ($K_D$) in the low nanomolar (N1-5-VHHm) to picomolar (N1-3-VHHm) range. N1-7-VHHm showed an approximately 10- to 100-fold lower affinity $K_D$ than N1-5-VHHm and N1-3-VHHm, respectively (Table 2). These binding affinities of N1-3-VHHm and N1-5-VHHm for N1rec resemble the affinities reported for a monomeric VHH that inhibits the activity of lysozyme (De Gest et al, 2006). Competitive surface plasmon resonance analysis also showed that prior binding of N1-3-VHHm to N1rec abolished subsequent binding of N1-5-VHHm and vice versa. On the other hand, N1-7-VHHm binding to N1rec was not affected by prior binding of N1-3-VHHm or N1-5-VHHm to N1rec (FIG. 2D). This observation suggests that N1-3-VHHm and N1-5-VHHm bind an overlapping epitope in N1rec, while the N1-7-VHHm targets a different epitope.

Figure 3:
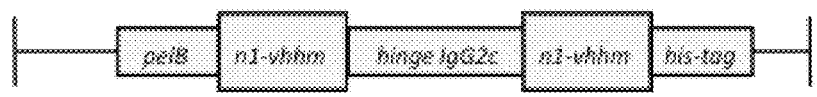
FIG. 3. Bivalent formats of the N1-3-VHH and N1-5-VHH, design and production. (A) Diagram of the expression cassette of the N1-VHHb, which consist of two n1-vhhm moieties in tandem, fused by a linker: pelB, signal peptide to the periplasmic compartment; n1-vhhm, n1-3/5-vhhm genes; hinge IgG2c, hinge sequence of the llama IgG2c immunoglobulin; his-tag, hexahistidine sequence. (B) Schematic diagram of the plant produced bivalent format N1-VHH-Fc T-DNA region in the binary vector pPhas: 3' ocs: 3' end of the octopine synthase gene; npt II, neomycin phosphotransferase II open reading frame; Pnos, nophaline synthase gene promoter; Pphas: β-phaseolin gene promoter; 5' utr: 5' UTR of arc5-I gene; SS: signal peptide of the *Arabidopsis thaliana* 2S2 seed storage protein gene; n1-vhh-fc: coding sequence of the N1-3/5/7-VHH-Fc; KDEL: ER retention signal; 3' arc, 3' flanking regulatory sequences of the arc5-I gene; RB and LB: T-DNA right and left border, respectively. (C) PCR amplification of the n1-vhhm (357 bp) and the n1-vhhb (763 bp) genes inserted in the pHEN6c vector, resolved in an agarose 1% gel. (D) BamHI digested empty "E" or n1-vhh-fc gene inserted pPhasGW.arc vector. The 1066 bp band indicates an n1-vhh-fc gene insert. (E) Cartoon representation of the 2 N1-VHH bivalent formats. The bacteria-produced N1-VHHb consists of two moieties in tandem of N1-VHHm linked by a llama IgG2c hinge of 17 amino acid residues. The plant-produced bivalent N1-VHH-Fc comprises two N1-VHH-Fc moieties, each consist of one N1-VHHm fused to a mouse IgG2a Fc, dimerized through a disulphide bond. (F) The llama IgG2c-derived hinge is sensitive to trypsin. Coomassie stained reducing SDS-PAGE of purified N1-3-VHHm, N1-5-VHHm, N1-3-VHHb and N1-5-VHHb incubated for 37 min at 37° C. in the presence or absence of 1 μg/ml or 10 μg/ml trypsin. The N1-VHHb molecules migrate at ca. 32 kDa, and the N1-VHHm and the cleavage products of N1-VHHb migrate as bands of ca. 17 kDa (arrows). (G) Coomasie stained reducing SDS-PAGE of the eluted fractions from a protein G column purification step using seed extracts of pPhas transformed *A. thaliana* T3 plants. The N1-VHH-Fc constructs migrate at ca. 42 kDa (arrow). A degradation product (*) of ca. 28 kDa corresponds to the Fc moiety only, as was confirmed by immunoblotting.
Figure 3:
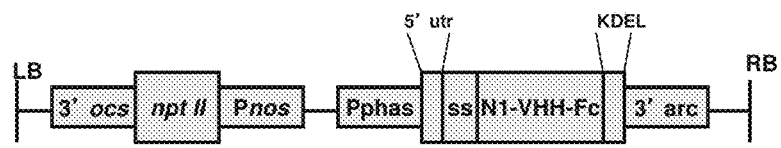
Figure 3:
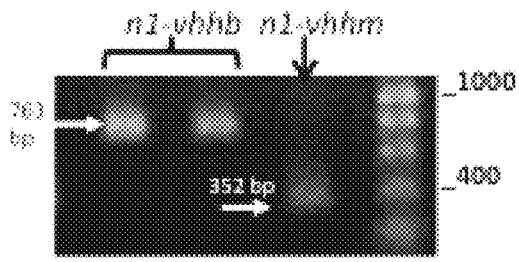
Figure 3:
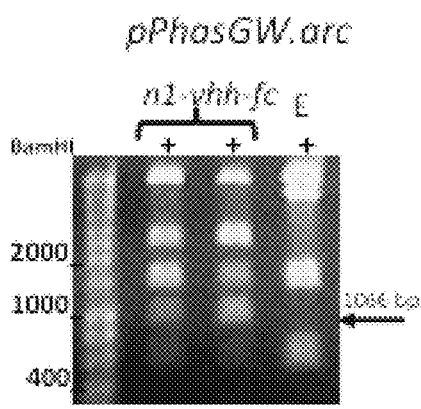
Figure 3:
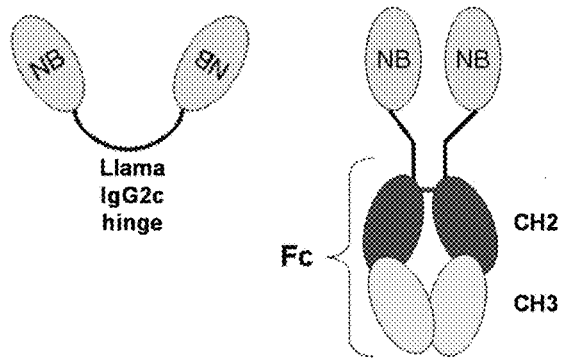
Figure 3:
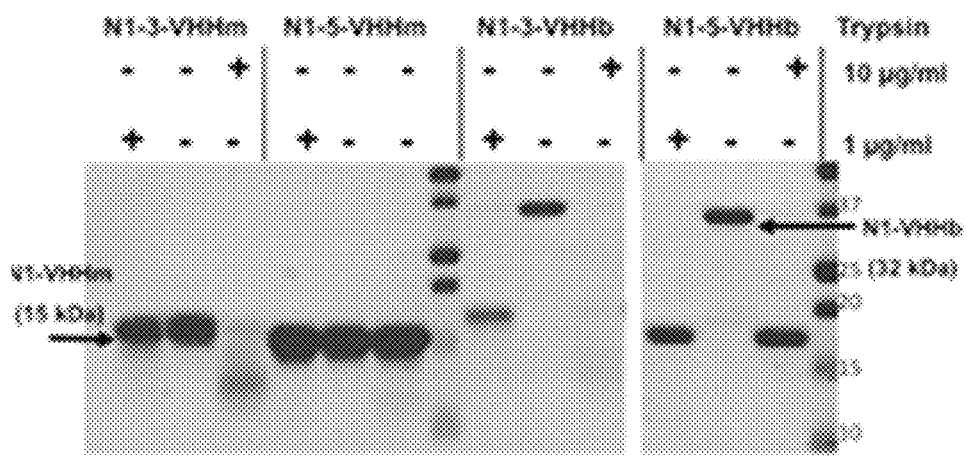
Figure 3:
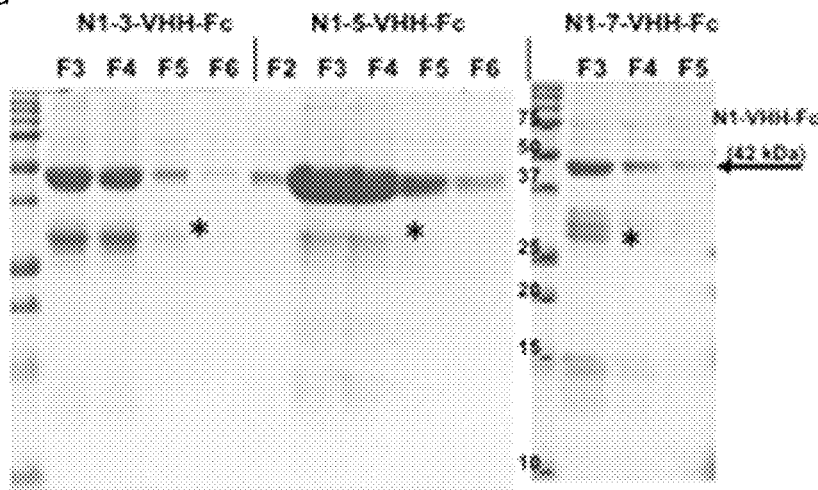

We next analysed the antiviral potential of the N1rec inhibitory VHHs, N1-3-VHHm and N1-5-VHHm. A/crested eagle/Belgium/09/2004 is a highly pathogenic H5N1 virus that we could not handle in our BLS2 facilities. Therefore, we used the laboratory strain NIBRG-14 virus, generated by reverse genetics and containing NA and HA (lacking the polybasic maturation sequence) segments derived from A/Vietnam/1194/2004 (see Materials and methods). The NA sequences of these two H5N1 viruses are highly homologous with only 13 amino acid sequence differences (FIG. 3A). In the presence of N1-3-VHHm or N1-5-VHHm the size and number of NIBR-14 plaques in monolayers of infected MDCK cells were reduced in a concentration dependent manner (Table 3, FIG. 3B). In contrast, the N1-7-VHHm did not affect the size or number of NIBRG-14 plaques in this assay (data not shown). These results suggest that the in vitro antiviral potential of the N1-3-VHHm and N1-5-VHHm depends of their NA-inhibitory activity.

TABLE 2

Binding and affinities of the N1-VHHm to N1rec.

| N1-VHHm | Binding to N1rec [a] | Inhibition of N1rec | $K_{on}$ ($M^{-1} \cdot s^{-1}$) | $K_{off}$ ($s^{-1}$) | $K_{KD}$ (M) [b] |
|---|---|---|---|---|---|
| 1 | + | + | | | |
| 2 | + | − | | | |
| 3 | + | + | $3.6E^{+6}$ | $1.3E^{-3}$ | $3.7E^{-10}$ |
| 4 | + | − | − | | |
| 5 | + | + | $1.2E^{+5}$ | $5.8E^{-4}$ | $4.7E^{-9}$ |
| 6 | + | + | | | |
| 7 | + | − | $4.4E^{+4}$ | $2.8E^{-3}$ | $6.3E^{-8}$ |
| 8 | + | − | | | |
| 9 | + | − | | | |
| 10 | + | − | | | |
| 11 | + | − | | | |
| 12 | + | − | | | |
| 13 | + | − | | | |

[a] N1rec, tetrameric recombinant N1 Neuraminidase.
[b] Equilibrium dissociation constant $K_D$ ($k_{off}/k_{on}$), association rate constant $k_{on}$ and dissociation constant $k_{off}$ determined by Surface Plasmon Resonance.

TABLE 3

N1-3-VHH and N1-5-VHH inhibition of the catalytic N1 NA activity ($IC_{50}$, nM)[a] and plaque size reduction in H5N1 virus infected cells (nM)[b]

| Format | N1rec[c] | Fold inc.[d] | NIBRG-14[e] | Fold inc. | H5N1 H274Y[f] | Fold inc. | NIBRG-23[g] | Fold inc. |
|---|---|---|---|---|---|---|---|---|
| N1-3-VHHm | 425.2 +/− 149.4 | — | 1844 +/− 344.3 | — | 6440 +/− 1247.0 | — | 4295 +/− 2835.4 | — |
| N1-5-VHHm | 374.9 +/− 118.5 | — | 848.5 +/− 380.2 | — | >26500 | — | 3492 +/− 2967.6 | — |
| N1-3-VHHb | 0.157 +/− 0.206 | 2708.3 | 7.6 +/− 3.0 | 240.9 | 52.2 +/− 36.8 | 123.3 | 24.6 +/− 31.9 | 174.6 |
| N1-5-VHHb | 0.69 +/− 0.231 | 543.3 | 14.5 +/− 11.1 | 58.2 | >707.5 | — | 23.6 +/− 3.8 | 148.0 |
| N1-3-VHH-Fc | 1.31 +/− 0.605 | 324.5 | 23.08[h] | 79.9 | 89.4 +/− 7.8 | 71.9 | 24.2 +/− 3.7 | 177.5 |
| N1-5-VHH-Fc | 1.49 +/− 0.746 | 251.6 | 28.14[h] | 30.2 | >17083 | — | 27.03 | 129.2 |
| Oseltamivir | 586.1 +/− 120.5 | — | 15030 +/− 10039 | — | >243000 | — | 73000[h] | — |

[a]Mean $IC_{50}$ of NA inhibition assay using the substrate 2'-(4-methylumbelliferyl)-a-D-N acetylneuraminic acid (MUNANA), using 160 ng of N1rec, in 3 independent experiments.
[b]Mean of duplicates concentration that reduced the 50% of plaque size and number compared to control VHH, in at least 2 independent experiments.
[c]N1rec, tetrameric recombinant N1 Neuraminidase.
[d]Potency fold increase of the bivalent format compared to the monovalent format.
[e]H5N1NIBRG-14.
[f]H5N1 H274Y.
[g]H5N1 NIBRG-23.
[h]Mean of single experiment.

Example 4: A Bivalent Format of the N1-VHH Enhances their NA-Inhibitory and Antiviral Activity It has been reported that multivalent formats of VHHs increases their affinity, by introducing avidity, for their target antigen and often also their functional activity (Hultberg, Temperton et al. 2011) (Ibanez, De Filette et al. 2011) (Schepens, Ibanez et al. 2011). For example, the introduction of avidity drastically decreased the dissociation constant ($K_{off}$) of the VHH molecules directed against lysozyme, and significantly improved their enzyme inhibitory activity as compared to their monovalent counterpart formats (Els Conrath, Lauwereys et al. 2001) (Hmila, Saerens et al. 2010). To increase the avidity of the N1-VHHm, two different bivalent formats were produced. As a first approach to obtain bivalent VHH, we used the llama IgG2c hinge (17 amino acid residues) as flexible linker to fuse 2 identical inhibitory N1-VHHm in a tandem configuration resulting in N1-3-VHHb and N1-5-VHHb (FIG. 3C). N1-3-VHHb and N1-5-VHHb were expressed and purified from E. coli and their in vitro NA inhibitory and antiviral activities were compared with those of their monovalent counterparts. We found that N1-3-VHHb and N1-5-VHHb displayed a 500-2000 fold enhanced N1rec inhibition activity as compared with the corresponding monovalent N1-3-VHHm and N1-5-VHHm format (Table 3). Surprisingly, in a plaque assay using NIBRG-14 virus infected MDCK cells, both N1-3-VHHb and N1-5-VHHb had an antiviral activity that was comparable to the levels of their monovalent counterparts (data not shown). We reasoned that the integrity of the bivalent format is necessary to present an enhanced antiviral potency in both N1-VHHb. However, in the plaque assay with H5N1 infected MDCK cells, exogenous trypsin is used to facilitate maturation of HA in newly produced virions to allow multicycle replication of the recombinant NIBRG-14 virus. We found that the dimerizing llama IgG2c hinge linker in the N1-VHHb was sensitive to trypsin cleavage (FIG. 3D). Therefore, in the presence of relatively low amounts of trypsin N1-3-VHHb and N1-5-VHHb were effectively severed into monovalent VHH. To circumvent the use of exogenously added trypsin we took advantage of the TMPRSS2 MDCK cells, which are stably transformed with the doxycyclin inducible serine protease TMPRSS2 and allow multicycle replication of influenza A viruses in the absence of trypsin (Bottcher, Freuer et al. 2009). Using monolayers of TMPRSS2 MDCK cells for infection with NIBRG-14, the antiviral effect of N1-3-VHHb and N1-5-VHHb was 240 and 58 fold increased, respectively, compared with their monovalent format (Table 3). These results obtained with N1-VHHb indicate that (i) there is a significantly enhanced NA-inhibitory and antiviral activity of both N1-VHHb compared with the N1-VHHm format and (ii) the 10-fold difference between the increase of the N1rec inhibition compared to the plaque assay, suggests than there are other factors that account for the in vitro antiviral effect of the N1-VHHb than just their inhibitory potential.

Example 5: Transgenic Plant Produced Bivalent N1-VHH (N1-VHH-Fc)

The previously described N1-VHH monovalent or bivalent molecules are relatively simply molecules that are stable and small sized, feasible for production in prokaryotic and yeast systems. For more complex protein molecules, other production platforms are available and have to be considered. We used a plant-based approach, with reported high-end yield results for recombinant antibodies (Van Droogenbroeck, Cao et al. 2007). In particular, targeting the protein of interest as a seed storage protein, we were able to produce a second bivalent N1-VHH format. For this, the n1-3-vhh, n1-5-vhh and the n1-7-vhh genes were fused to the sequence encoding the hinge and Fc tail of a mouse IgG2a (n1-vhh-fc). The resulting N1-VHH-Fc consists of two identical N1-VHH-Fc moieties linked by a disulphide bridge (FIG. 3C). These n1-vhh-fc constructs were cloned into the binary vector pPhas as a T-DNA expression cassette (FIG. 3E). Subsequently, transgenic Arabidopsis thaliana plants were generated by Agrobacterium-mediated floral dip transformation. Seed extract of segregating T3 Arabidopsis clones were used for screening to identify the highest expressers of the recombinant dimeric protein N1-VHH-Fc (data not shown). Coomassie stained, reducing SDS-PAGE analysis showed that the N1-VHH-Fc monomers migrated at ca. 42 kDa band (FIG. 3F). We also found a good correlation between the expression level of the N1-VHH-Fc and the NA inhibitory activity in crude seed extracts from different T3 transformants (data not shown). The N1-3-VHH-Fc, N1-5VHH-Fc and N1-7-VHH-Fc were purified from seed extracts by protein G affinity chromatography (FIG. 3F). We found stronger N1 rec inhibition and in vitro antiviral activity by N1-3-VHH-Fc and N1-5-VHH-Fc compared with the monovalent N1-3-VHHm and N1-5-VHHm (Table 3). Nevertheless, the N1-3-VHHb and N1-5-VHHb still proved to be 2 to 8 times more potent in NA inhibition compared with N1-3-VHH-Fc and N1-5-VHH-Fc (Table 3). In addition, inhibition of replication of NIBRG-14 virus by either N1-3-VHH-Fc or N1-5-VHH-Fc was 80- and 30-fold stronger, respectively, compared with their monovalent counterparts (Table 3). We conclude that the in vitro NA inhibition and antiviral activity against NIBRG-14 virus is strongly enhanced by bivalent N1-VHH formats with the highest improvement observed for tandemly linked copies of VHH molecules.

Example 6: In Vitro Antiviral Activity of N1-VHH Against Clade 2.2, Oseltamivir-Resistant H5N1 Virus and Pandemic H1N1 2009 Virus The NA derived from A/crested eagle/Belgium/01/2004 belongs to the clade 1 of the H5N1 NAs, which also includes NA of the NIBRG-14 (derived from A/Vietnam/1194/2004).H5N1 NA derived from A/turkey/Turkey/01/2005 belongs to the clade 2.2. These 3 different NAs shared a high homology between them (>95%) and were used as targets in the present study (FIG. 3A). Although the number of laboratory confirmed human cases of H5N1 virus infection remain limited, it appears that clade 2 H5N1 viruses comprise a majority of these zoonotic infections with highly pathogenic avian influenza viruses. We therefore evaluated the antiviral potential of N1-3-VHH and N1-5-VHH in the three formats available (i.e. monovalent, bivalent without and with Fc) against the clade 2.2 virus NIBRG-23. Monovalent N1-3-VHHm and N1-5-VHHm reduced in vitro growth of NIBRG-23 virus on MDCK with an $IC_{50}$ in the low micromolar range (Table 3). Both bivalent formats of these NA-inhibitory VHH, (N1-3-VHHb, N1-5-VHHb, N1-3-VHH-Fc and N1-5-VHH-Fc) displayed an approximately 150-fold higher in vitro antiviral activity against this clade 2 virus as judged by a plaque size reduction assay, compared with their monovalent counterparts. Based on these findings, we conclude that the two NA-inhibitory VHH can inhibit H5N1 viruses representative for clade 1 and clade 2 with a comparable efficiency in vitro, suggesting that they target an epitope that is shared in the NA of these viruses.

Oseltamivir-resistant influenza viruses frequently emerge and spread in the human population. Several mutations had been reported to contribute to oseltamivir resistance but among these the mutation H274Y (N2 numbering) is the most commonly found in oseltamivir resistant viruses (Wang, Tai et al. 2002). Therefore, we wanted to determine if our N1-3-VHHb, N1-5-VHHHb, N1-3-VHH-Fc and N1-5-VHH-Fc would be active against an oseltamivir-resistant H5N1 virus that carries this mutation. We used a reverse genetics method (Hoffmann, Neumann et al. 2000) to generate a clade 1 H5N1 virus (harbouring the H274Y mutation in NA derived from A/crested eagle/Belgium/09/2004, the HA segment from NIBRG-14 and the remaining 6 segments from PR/8), resulting in the H5N1 H274Y virus used in this study. Given that all of our formats of N1-3-VHH and N1-5-VHH performed similar in biochemical and in vitro antiviral activity assays, we were surprised to observe that only the N1-3-VHH in monovalent and both bivalent formats, but not any format of N1-5-VHH, reduced growth of oseltamivir-resistant H5N1 H274Y virus (Table 3). Compared to NIBRG-14 as a target, the H5N1 H274Y $IC_{50}$ values were 3 to 7-fold higher, but still in the low nM range. Even though the competitive surface Plasmon resonance experiment suggested that the epitope in NA is shared for both N1-3-VHHm and N1-5-VHHm, the contact residues necessary for their binding are not the same. The H274Y mutation seems to be sufficient to abolish the in vitro antiviral effect of the N1-5-VHH formats during the infection with the H5N1 H274Y mutant virus used here. We conclude that NA-specific VHH, such as N1-3-VHHm, N1-3-VHHb and N1-3-VHH-Fc can inhibit growth of H5N1 viruses in vitro, even if such viruses are oseltamivir resistant.

Figure 4:
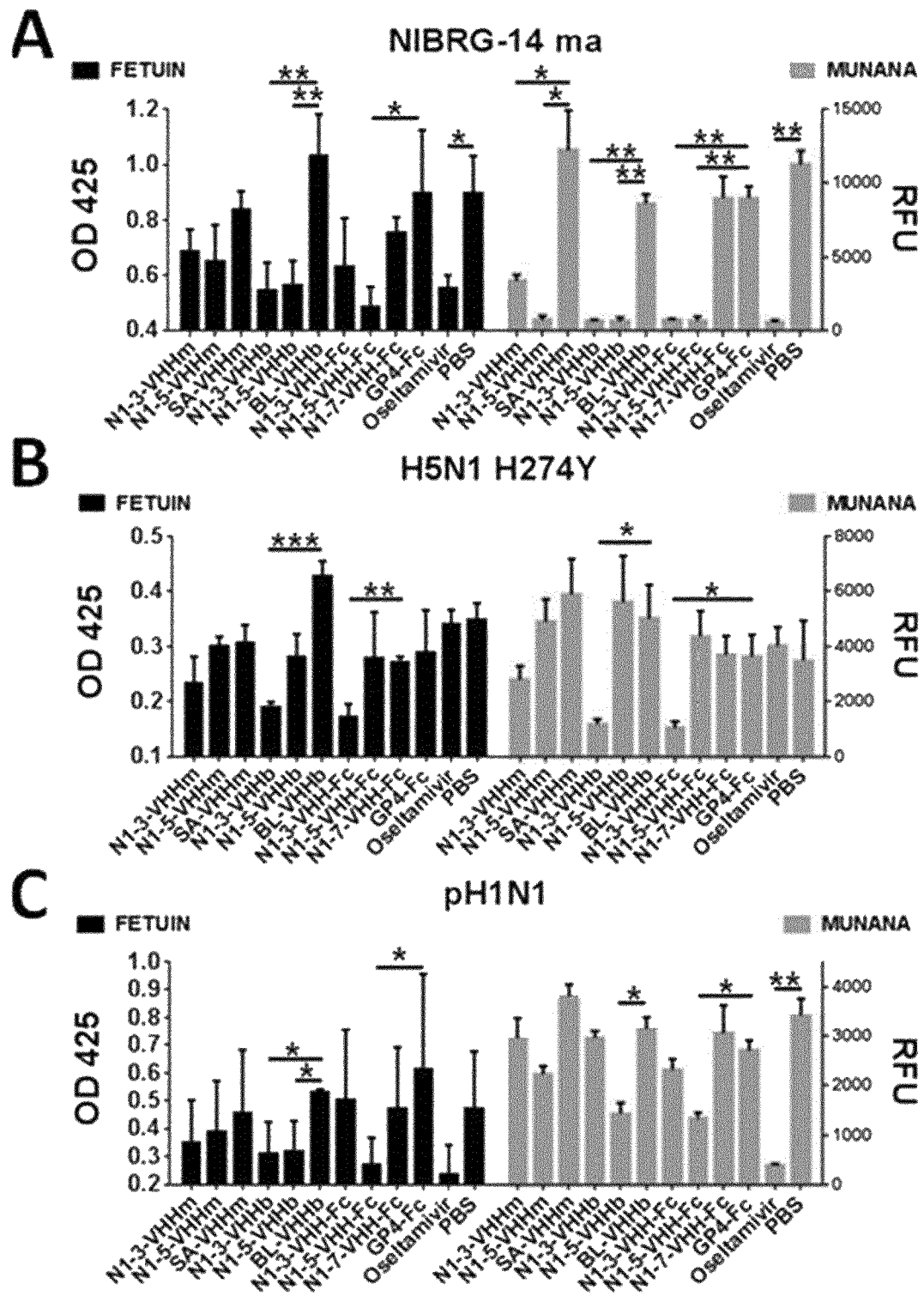
FIG. 4. N1-VHH inhibits NA activity from NIBRG-14 ma, H5N1 H274Y and pH1N1 virions. We used as substrates fetuin (left) and MUNANA (right). A. NIBRG-14 ma NA inhibition. B. H5N1 H274Y Oseltamivir-resistant NA activity inhibition. C. Pandemic H1N1 2009 NA activity inhibition. SA-VHHm, monovalent VHH directed against seed storage albumin; BL-VHHb, bivalent VHH directed against bacterial beta lactamase; GP4-Fc, coronavirus GP4 protein fused to mouse IgG2a Fc. For comparing the significance among different groups, t test was used (*$P<0.05$; **$P<0.01$). Results are representative of two independent experiments.

Next, we tested the antiviral potential of all N1-3-VHH and N1-5-VHH formats against a pandemic H1N1 2009 virus isolate (pH1N1). We used fetuin and MUNANA (AVINA assay) as two alternative substrates for virion-associated NA activity. Using NIBRG-14 ma, and based on MUNANA hydrolysis, monovalent N1-3-VHHm and N1-5-VHHm had significant inhibitory activity, compared with the negative controls SA-VHHm ($P<0.05$) and PBS ($P<0.01$), although this tendency was not significant in the fetuin assay (FIG. 4A). We found that the bivalent molecules N1-3-VHHb, N1-5-VHHb, N1-3-VHH-Fc and N1-5-VHH-Fc significantly inhibited NA activity for both substrates ($P<0.01$, FIG. 4A).

In line with our previous results using H5N1 H274Y IAV, only N1-3-VHHb and N1-3-VHH-Fc showed NAI activity using both substrates. ($P<0.05$, or $P<0.01$) (FIG. 4B). N1-5-VHHb and N1-5-VHH-Fc showed inhibitory potential against pH1N1 in both assays. ($P<0.05$) (FIG. 4C). These AVINA and fetuin results for NIBRG-14 ma and H5N1 H274Y NA are in accordance with the N1rec inhibition and the plaque size reduction assays mentioned before (Table 2). In addition, both bivalent N1-5-VHHb formats inhibited pH1N1 virion-associated NA activity, suggesting a degree of intra subtype inhibitory effect of the N1-VHHs.

Figure 5:
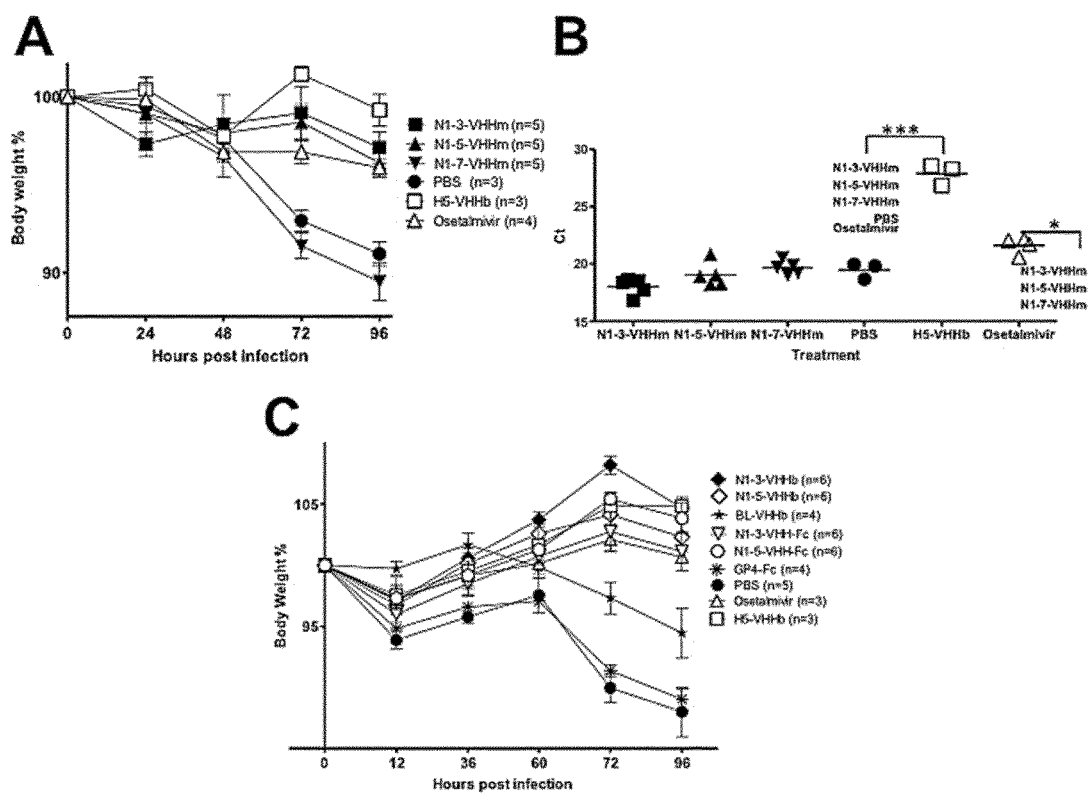
FIG. 5. Single intranasal administration of N1-3-VHHm, N1-5-VHHm, N1-3-VHHb and N1-5-VHHb decrease the morbidity during the first four days after challenge with H5N1 virus. A. Groups of 6-8 week-old BALB/c mice were given 100 μg of indicated VHH, administered intranasally at 4 hours before challenge with 1 LD50 of NIBRG-14ma virus. Thirty μg of intranasal administered H5-VHHb and daily oral administration of Oseltamivir (45/kg/day, from 4 hrs before challenge) were included as positive controls. Body weight was monitored daily after challenge and expressed as the percentage of initial body weight. The groups of mice treated with N1-3-VHHm and N1-5-VHHm displayed significantly less morbidity than the groups treated with PBS ($P<0.001$), N1-7-VHHm ($P<0.001$) at 72 and 96 hours post infection. B. Mice were sacrificed on day 4 after challenge and lung homogenates were prepared. A viral genome specific RT-qPCR was used as readout for the viral load. The obtained Ct values for the individual mice are plotted and a horizontal line indicates the mean. The Ct value H5-VHHb group was significantly different (indicative for lower virus load), compared to all other groups (***: $P<0.001$). The Oseltamivir treated group was only slightly different from the groups treated with the N1-3-VHHm, N1-5-VHHm and N1-7-VHHm (*: $P<0.05$). C. The bivalent format of the N1-3-VHH and N1-5-VHH increases the potency to reduce the morbidity in H5N1-challenged mice. Four hours before challenge with 1 LD50 of NIBRG-14 ma virus, groups of BALB/c mice were treated intranasally with 60 μg of N1-3-VHHb, 60 μg of N1-5-VHHb, 60 μg of BL-VHHb, 84 μg of N1-3-VHH-Fc, 84 μg of N1-5-VHH-Fc or 84 μg of GP4-Fc. Mice treated with neutralizing H5-VHHb (30 μg) or Oseltamivir (45 mg/kg/day, daily by gavage) were included as positive controls. The groups treated with both bivalent formats of the N1-3-VHH and N1-5-VHH were significantly different compared with groups treated with: BL-VHHb and GP4-Fc at 60 hpi ($P<0.05$), 72 and 96 hpi ($P<0.001$); PBS, 36 and 60 hpi ($P<0.05$), and at 72 and 96 hpi ($P<0.001$).

Example 7: The Treatment with N1-3-VHHm and N1-5-VHHm Reduces Morbidity in H5N1-Challenged Mice We next evaluated the in vivo antiviral effect of the NA-specific VHH. In a first experiment we administered intranasally 100 µg of N1-3-VHHm, N1-5-VHHm, and N1-7-VHHm to BALB/c mice at 4 hours before challenge with 4 $LD_{50}$ of mouse-adapted NIBRG-14 virus (NIBRG-14ma). As positive controls we included a group of mice that received 30 µg of H5-VHHb, a bivalent NIBRG-14ma-neutralizing VHH (Ibanez, De Filette et al. 2011) as well as daily oral administration of oseltamivir, at a high dose (45 mg/kg/day). The body weight was followed daily, and the groups treated with the inhibitory N1-3-VHHm or N1-5-VHHm showed a significant difference in morbidity at 72 and 96 hours after infection, compared with the groups treated with the N1-7-VHHm and PBS ($P<0.001$) (FIG. 5A). Four days after infection, the mice were sacrificed to determine lung virus titers. Assessment of the lung virus load by endpoint dilution in a TCID50 assay, revealed that all mice had a high and comparable virus load between −4.75 to −6.48 $TCID_{50}$/ml in the lung homogenates (including the oseltamivir treated group)(data not shown). We therefore decided to quantify the amount of viral RNA in the lung homogenates using a genome strand-specific RT-qPCR method. Except for the samples derived from the H5-VHHb treated mice, all the N1-VHH treated groups showed high viral RNA levels at 96 h after infection, comparable to those in the PBS-treated group, even so for the high oseltamivir dose treated mice, which difference with the rest of the groups was significant (P<0.05) (FIG. 5B). We conclude that intranasal administration of monovalent N1-3-VHHm and N1-5-VHHm prevents body weight loss after challenge with NIBR-14 virus during the early stage of infection.

Example 8: Bivalent Formats of N1-VHHb Protect Against H5N1 Challenge

The in vitro results indicated that the bivalent formats of the NA-inhibitory VHH increased their potency against the tested H5N1 viruses at least 30-fold compared to the monovalent ones (Table 3). We therefore assessed if this increased antiviral effect would also be reflected in an in vivo challenge experiment. We first determined the protective potential during the early stages of viral infection. Four hours prior to challenge with 4 $LD_{50}$ of NIBRG-14 groups of BALB/c mice were intranasally given 60 µg of N1-3-VHHb, 60 µg of N1-5-VHHb, 60 µg of BL-VHHb (a bivalent VHH directed against the irrelevant bacterial target β-lactamase), 84 µg of N1-3-VHH-Fc, 84 µg of N1-5-VHH-Fc or 84 µg of GP4-Fc (a plant-produced Coronavirus-Fc fusion protein with an IgG2a Fc moiety, used here as an irrelevant control). Treatment with N1-3-VHHb or with N1-3-VHH-Fc significantly improved morbidity at 72 and 96 h after infection compared with the negative control groups GP4-Fc and PBS (P<0.001). This protection against weight loss was comparable to that observed with the positive controls (H5-VHHb and Oseltamivir) (FIG. 5C). On the other hand, treatment with the bivalent formats of N1-5-VHH resulted in a decrease in morbidity that was significant at 60, 72 and 96 hpi compared with the negative controls (P<0.001) (FIG. 5C). Determination of the lung virus load on day 4 after challenge by a $TCID_{50}$-based assay using lung homogenates from sacrificed mice, revealed that all challenged groups, except the H5-VHHb-treated mice (no virus detectable), had a comparable lung virus load (data not shown). Taken together, both bivalent formats (tandem repeats and Fc-mediated) of N1-inhibitory N1-3-VHH and N1-5-VHH improve protection during the first four days following NIBRG-14 challenge.

Figure 6:
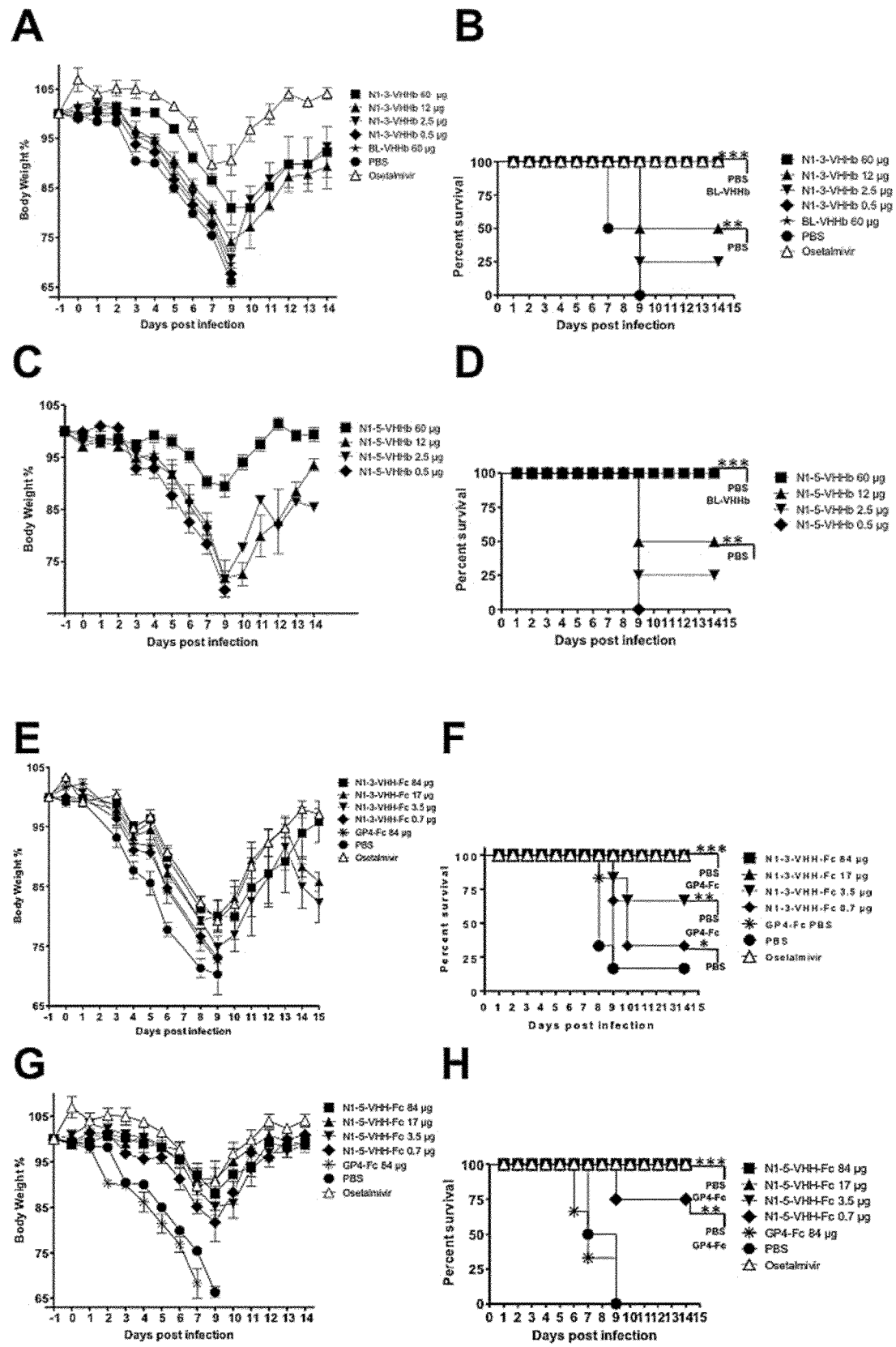
FIG. 6. The N1-VHH bivalent formats protect against morbidity and mortality in a dose-dependent way in H5N1-challenged mice. Groups of 4 BALB/c mice were given the indicated amount of N1-VHH and administered 24 hours before challenge with 1 LD50 of NIBRG-14 ma virus. One group of mice was treated with one dose of Oseltamivir (45 mg/day/kg) as positive control at 24 hrs before challenge, followed by daily boost from 6-14 days after challenge. A boost was given at 6 dpi only to the highest doses of each treatment, including the Oseltamivir. A. The group of mice treated with 60 μg of N1-3-VHHb presented significant increase in morbidity compared to the Oseltamivir group at: 10-11 dpi ($P<0.001$), 12-13 dpi ($P<0.01$) and 14 dpi ($P<0.05$). The difference of the morbidity between the different N1-3-VHHb treated groups was not significant ($P>0.05$). B. The survival of the N1-3-VHHb 60 μg group was 100%, highly significantly different from the control groups BL-VHHb 60 μg and PBS (*, $P<0.001$). In the group treated with 12 μg N1-3-VHHb survival was 50%, but still significantly different from the PBS groups (, $P<0.01$). The survival of the groups treated with N1-3-VHHb 2.5 μg (25%) and 0.5 μg (0%) was not different to the control groups ($P>0.05$). C. The morbidity of the N1-5-VHHb 60 μg treated group was different from the N1-5-VHHb 12, 2.5 and 0.5 μg groups at days 10-14 ($P<0.001$), but not different from the Oseltamivir group ($P>0.05$). D. The survival and significance of the N1-5-VHHb treated groups was similar to the N1-3-VHHb treatment in C. dpi, days post infection. E. Groups of 6 BALB/c mice were treated with different amounts of N1-3-VHH-Fc, but the difference in morbidity was not significant between them or compared with the Oseltamivir treated group ($P>0.05$). F. The survival and statistical significance of the N1-3-VHH-Fc treated groups treated with different doses and compared to the control groups PBS and GP4-Fc 84 μg: N1-3-VHH-Fc 84 μg and 17 μg, 100% (both *, $P<0.001$); N1-3-VHH-Fc 3.5 μg, 66.6% (both, , $P<0.01$); 0.7 μg, 33.3% (PBS, $P<0.05$,). G. The morbidity of the groups treated with N1-5-VHH-Fc was not significantly different between them and compared to the Oseltamivir treated group. H. The survival of the groups treated with N1-5-VHH-Fc 84, 17 or 3.5 μg was 100%, being highly significantly different from survival in the groups GP4-Fc 84 μg and PBS (*, $P<0.001$). The treatment with N1-5-VHH-Fc 0.7 μg resulted in a survival of 75%, significantly different from the groups GP4-Fc 84 μg and PBS (, $P<0.01$).

Example 9: Bivalent NA Inhibitory VHH Protection Against a Lethal Challenge with H5N1 Virus is Dose-Dependent In order to probe if mice that have been challenged with 4 $LD_{50}$ of NIBRG-14ma virus can be rescued by prior administration of N1-3-VHHb, N1-3-VHH-Fc, N1-5-VHHb or N1-5-VHH-Fc we followed the morbidity and mortality over a 2-week period. For this, we focused on the bivalent formats and first assessed their protective efficacy in a dose-response experiment. Groups of four BALB/c mice where treated intranasally with 60, 12, 2.5 or 0.5 µg of N1-3-VHHb or N1-5-VHHb. In parallel a group was treated by oral administration of oseltamivir (45 mg/kg/day), and a boost of oseltamivir were given at 6-14 days after challenged. In addition, one group of mice was treated with 60 µg of BL-VHHb or with PBS prior to challenge. In this experiment mice that had received 60 µg of N1-3-VHHb, N1-5-VHHb or BL-VHHb prior to challenge received a second intranasal dose with 60 µg of the same bivalent VHH at day 6 after challenge. All mice from the PBS and BL-VHHb treatment groups succumbed after challenge at 9-10 days after challenged. In contrast, oseltamivir and high dose (60 µg) intranasal treatment with N1-3-VHHb or N1-5-VHHb displayed clear body weight loss following challenge (FIGS. 6A and C), but protected the mice against lethality (FIGS. 6B and D). Surviving N1-3-VHHb 60 µg treated group, but not the N1-5-VHHb 60 µg treated group, displayed a significant delay in recovery from weight loss after challenge compared with the oseltamivir treated group (FIGS. 6A and C). A single intranasal dose of 12 µg or 2.5 µg of either N1-3-VHHb or N1-5-VHHb provided partial protection against mortality but failed to reduce morbidity (FIG. 6A-D).

We next evaluated protection against a potentially lethal NIBRG-14ma challenge by prior single intranasal administration of the plant-produced N1-3-VHH-Fc and N1-5-VHH-Fc formats. Eighty four and 17 µg of N1-3-VHH-Fc as well as oseltamivir treatment provided full protection against NIBRG-14 challenge but the survival of the mice treated with 3.5 and 0.7 µg was dose-dependent (FIGS. 6F and H). Nevertheless this protection was associated with significant body weight loss in all dosing used, including the oseltamivir group (FIGS. 6E and G). All PBS and GP4-Fc treated animals died after challenge by day 9 after challenge. On the other hand, the body weight loss was less severe in the treatment with all N1-5-VHH-Fc treated groups, and only the group treated with 0.7 µg failed to show a survival of 100% (FIGS. 6G and H). Finally, when comparing the protective efficacy of the two bivalent formats of N1-3-VHH and N1-5-VHH, it appears that the Fc moiety in the N1-VHH-Fc formats provides an extra protective effect against morbidity and mortality following NIBRG-14ma challenge. This increased protective potential correlates with the somewhat higher NA inhibitory activity in a biochemical assay using purified N1rec but is not reflected in the plaque number/size reduction assay (Table 3). Taken together, we conclude that bivalent formats of N1-3-VHH and N1-5-VHH can protect mice against a potentially lethal challenge with an H5N1 virus, although this protection does not eliminate completely morbidity following challenge.

Figure 7:
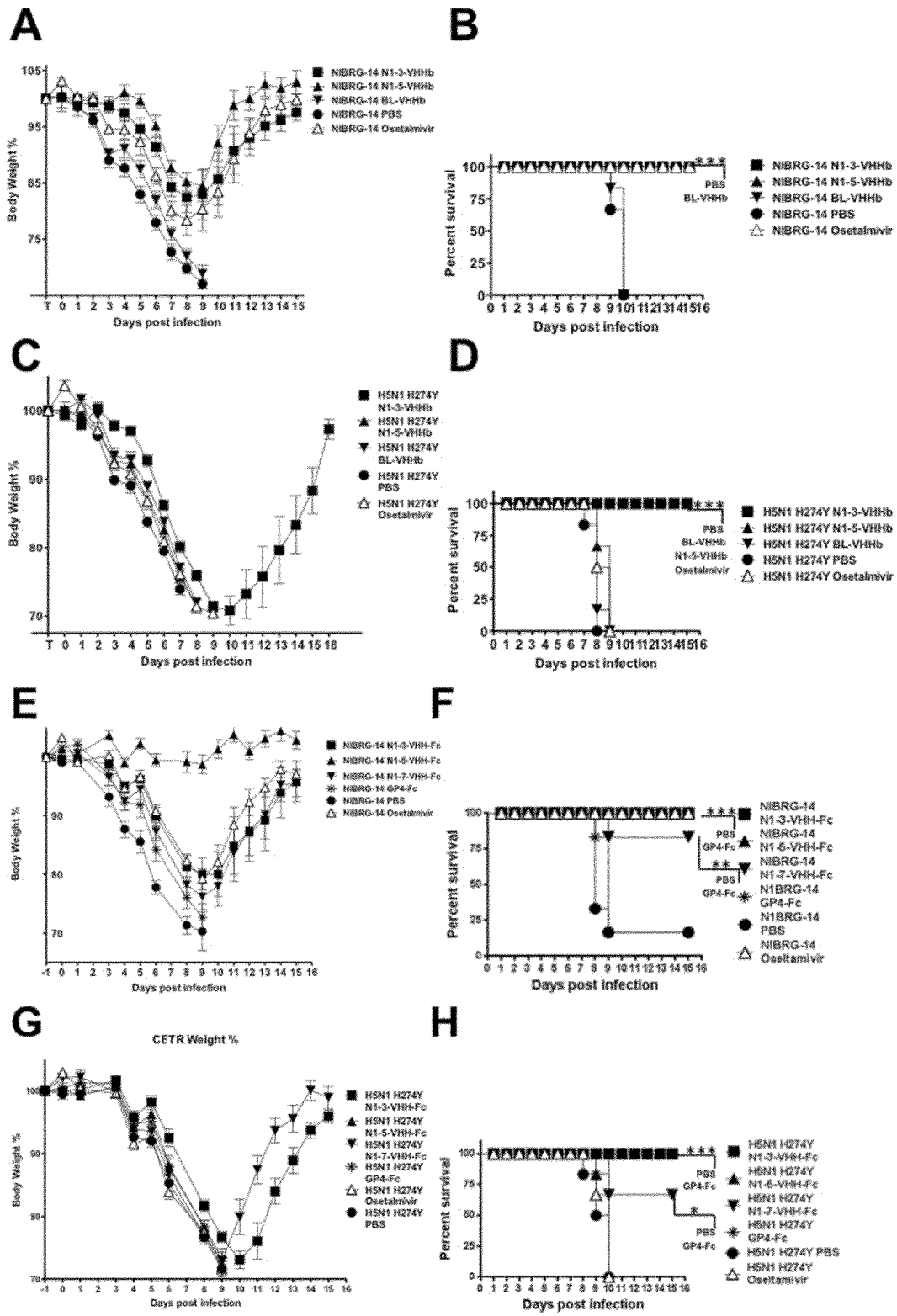
FIG. 7. Treatment with N1-3-VHHb or N1-3-VHH-Fc, but not with N1-5-VHHb/N1-5-VHH-Fc, rescues mice from a H5N1 H274Y 1 LD50 challenge. Twenty-four hours before challenge with 1 LD50 of NINRG-14 or H274Y H5N1 virus, groups of 6 BALB/c were given: 60 μg of N1-3-VHHb, N1-5-VHHb or BL-VHHb; 84 μg of the N1-3-VHH-Fc, N1-5-VHH-Fc or GP4-Fc. Groups of 6 mice were treated with Oseltamivir (1 mg/day/kg) as positive control. A. There was not significant difference in the morbidity between the groups treated with N1-3-VHHb and N1-5-VHHb, or compared to the Oseltamivir group during the NIBRG-14 infection ($P>0.05$). B. In NIBRG-14 infected mice, the N1-3-VHHb, N1-5-VHHb and Oseltamivir treated groups showed a survival of 100%, being significantly different from the control groups BL-VHHb and PBS (*, $P<0.001$). C. The morbidity of H5N1 H274Y treated groups was severe, with all groups close to a body weight loss of 70%, only the N1-3-VHHb treated group showed an increase of body weight at 10 dpi. D. The treatment with N1-3-VHHb rescued all the H5N1 H274Y infected mice (survival of 100%), with high statistical significance compared with the rest of the groups (*, P<0.001). The N1-5-VHHb and Oseltamivir treatments failed to rescue H274Y infected mice. E. In NIGRG-14 infected mice, the difference in morbidity of the N1-5-VHH-Fc group compared with the N1-3-VHH-Fc, N1-7-VHH-Fc, GP4-Fc or Oseltamivir groups is significant at days: 8-13 dpi (P<0.001) and 14 dpi (P<0.01). F. The treatment of N1-3-VHH-Fc, N1-5-VHH-Fc and Oseltamivir in NIBRG-14 infected mice results in a highly significant (*, P<0.001) survival of 100%. The group treated with N1-7-VHH-Fc presented a survival of 83.3%, being significantly different compared to PBS (, P<0.01) and GP4-Fc (P<0.05). G. In the same way as in C., the body weight loss was severe in the H5N1 H274Y infected mice, but the groups treated with N1-3-VHH-Fc and N1-7-VHH-Fc presented an increased in the body weight at 10 dpi. H. In H5N1 H274Y infected mice, the survival of the groups treated with N1-3-VHHb and N1-7-VHH-Fc was significant, 100% (*, P<0.001) and 66.6% (, P<0.05), respectively. The N1-5-VHH-Fc and Oseltamivir treatments failed to rescue H274Y infected mice.
Figure 8:
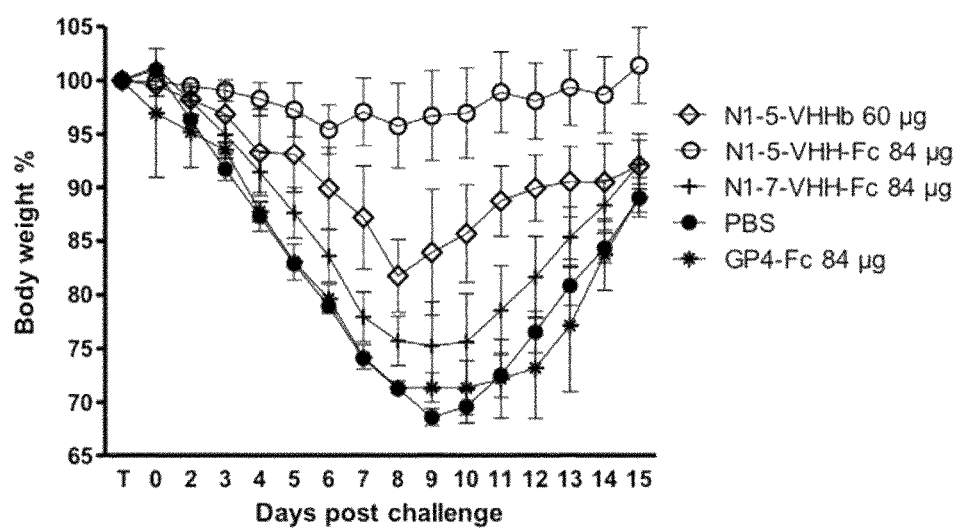
FIG. 8. The treatment with N1-5-VHHb and N1-5-VHH-Fc decrease significantly the morbidity in N-14 challenged FcγRI/FcγRIII K.O. mice. Twenty-four hours before challenge with 4 LD50 of NINRG-14 virus, groups of 4 FcγRI/FcγRIII K.O. mice were given: 60 µg of N1-5-VHHb or 84 µg of the N1-5-VHH-Fc/N1-7-VHH-Fc/GP4-Fc. The N1-5-VHH-Fc treated group showed no morbidity and was statistically different to: the N1-5-VHHb group at 8 dpi (P<0.01) and 9 dpi (P<0.05); the N1-7-VHH-Fc group at 7-11 dpi (P<0.001), 12 dpi (P<0.01) and 13 dpi (P<0.05). The morbidity of the N1-5-VHHb treated group was statistically different to: GP4-Fc group, at 9 dpi (P<0.05), 10 pdi (P<0.01), 11-12 dpi (P<0.001) and 13 dpi (P<0.05); PBS group, at 9-10 dpi (P<0.01), 11 dpi (P<0.01) and 12 dpi (P<0.05). The morbidity between the N1-5-VHHb and the N1-7-VHH-Fc groups was not statistically different.

Example 10: N1-3-VHHb and N1-3-VHH-Fc Protect Against Challenge with an Oseltamivir-Resistant H5N1 Virus In vitro analysis demonstrated that N1-3-VHH but not N1-5-VHH in monovalent or bivalent format could reduce growth of oseltamivir-resistant H5N1 H274Y virus (Table 3). Groups of 6 BALB/c mice received 30 µg of N1-3-VHHb, N1-5-VHHb or BL-VHHb by intranasal administration 24 hours before challenge with 4 $LD_{50}$ of either NIBRG-14 or H5N1 H274Y virus. A PBS-recipient group was included as negative control. In parallel, a group was treated by daily oral administration of oseltamivir (1 mg/kg/day), a dose that has been reported to protect laboratory mice against challenge with an H5N1 virus (Govorkova, Leneva et al. 2001). All N1-3-VHHb, N1-5-VHHb and oseltamivir treated mice survived challenge with NIBRG-14 virus whereas PBS and BL-VHHb recipient mice succumbed after challenge (FIGS. 7A and B). This result demonstrates that a single intranasal administration of N1-3-VHHb of N1-5-VHHb is sufficient to protect against a subsequent (24 h later) potentially lethal challenge with an H5N1 virus that has an antigenically matching NA. Again all surviving mice suffered from substantial but transient weight loss after challenge (FIG. 7B). From the mice that had been similarly treated as above but challenged with H5N1 H274Y virus, only those that had received N1-3-VHHb prior to challenge survived. All other groups, including those that had been treated with an oseltamivir dose that fully protected against NIBRG14-ma challenge, died following challenge with H5N1 H274Y virus (FIGS. 7C and D). Finally, we evaluated the effect of prior intranasal instillation of bivalent Fc formatted N1-3-VHH-Fc, N1-5-VHH-Fc and now also N1-7-VHH-Fc in our lethal challenge model. We again included PBS and oseltamivir treatment groups as well as GP4-Fc recipients. Following challenge with 4 $LD_{50}$ of NIBRG-14ma, all mice except 1 mouse in the PBS and 1 mouse in the GP4-Fc group died. In the N1-7-VHH-Fc group, only 1 of 6 mice died after challenge. In contrast, all mice in the N1-3-VHH-Fc, N1-5-VHH-Fc and oseltamivir groups survived this challenge and all displayed significant body weight loss, except for the mice that had received N1-5-VHH-Fc that appeared to be fully protected from morbidity following NIBRG-14ma challenge (FIGS. 7E and F). Challenge with H5N1 H274Y virus proved lethal to all mice except for those that had been treated in advance with N1-3-VHH-Fc (all mice survived) or N1-7-VHH-Fc (4 out of 6 mice survived) although all animal suffered from substantial body weight loss after challenge (FIGS. 7G and H). We conclude that bivalent NA-specific VHH can protect against a potentially lethal challenge with oseltamivir-resistant H5N1 virus.

REFERENCES

Arbabi Ghahroudi, M., A. Desmyter, et al. (1997). "Selection and identification of single domain antibody fragments from camel heavy-chain antibodies."*FEBS Lett* 414(3): 521-526.

Bottcher, E., C. Freuer, et al. (2009). "MDCK cells that express proteases TMPRSS2 and HAT provide a cell system to propagate influenza viruses in the absence of trypsin and to study cleavage of HA and its inhibition."*Vaccine* 27(45): 6324-6329.

Chotpitayasunondh, T., K. Ungchusak, et al. (2005). "Human disease from influenza A (H5N1), Thailand, 2004." *Emerging infectious diseases* 11(2): 201-209.

Clough, S. J. and A. F. Bent (1998). "Floral dip: a simplified method for *Agrobacterium*-mediated transformation of *Arabidopsis thaliana*." *The Plant journal: for cell and molecular biology* 16(6): 735-743.

De Genst, E., K. Silence, K. Decanniere, K. Conrath, R. Loris, J. Kinne, S. Muyldermans, and L. Wyns. (2006). "Molecular basis for the preferential cleft recognition by dromedary heavy-chain antibodies". *Proceedings of the National Academy of Sciences of the United States of America* 103: 4586-4591.

De Jaeger, G., S. Scheffer, et al. (2002). "Boosting heterologous protein production in transgenic dicotyledonous seeds using *Phaseolus vulgaris* regulatory sequences."*Nature biotechnology* 20(12): 1265-1268.

de Jong, M. D., C. P. Simmons, et al. (2006). Fatal outcome of human influenza A (H5N1) is associated with high viral load and hypercytokinemia. *Nat Med.* 12: 1203-1207.

Dolan, B. P., L. Li, et al. (2010). "Defective ribosomal products are the major source of antigenic peptides endogenously generated from influenza A virus neuraminidase."*Journal of immunology* 184(3): 1419-1424.

Els Conrath, K., M. Lauwereys, et al. (2001). "Camel single-domain antibodies as modular building units in bispecific and bivalent antibody constructs."*J Biol Chem* 276(10): 7346-7350.

Goto, H. and Y. Kawaoka (1998). "A novel mechanism for the acquisition of virulence by a human influenza A virus."*Proceedings of the National Academy of Sciences of the United States of America* 95(17): 10224-10228.

Govorkova, E. A., I. A. Leneva, et al. (2001). "Comparison of efficacies of RWJ-270201, zanamivir, and oseltamivir against H5N1, H9N2, and other avian influenza viruses."*Antimicrobial agents and chemotherapy* 45(10): 2723-2732.

Gubareva, L. V., M. S. Nedyalkova, et al. (2002). "A release-competent influenza A virus mutant lacking the coding capacity for the neuraminidase active site."*The Journal of general virology* 83(Pt 11): 2683-2692.

Harbury, P. B., T. Zhang, et al. (1993). "A switch between two-, three-, and four-stranded coiled coils in GCN4 leucine zipper mutants."*Science* 262(5138): 1401-1407.

Hassantougighi, A., H. Zhang, M. Sandbulte, J. Gao, J. Manischewitz, L. King, H. Golding, T. M. Straight and M. C. Eichelberger (2010). "A practical influenza neutralization assay to simultaneously quantify heamgglutinin and neuraminidase-inhibiting antibody responses."*Vaccine* 28: 790-797.

Herfst, S., E. J. Schrauwen, et al. (2012). "Airborne transmission of influenza A/H5N1 virus between ferrets."*Science* 336(6088): 1534-1541.

Hmila, I., D. Saerens, et al. (2010). "A bispecific nanobody to provide full protection against lethal scorpion envenoming."*Faseb J* 24(9): 3479-3489.

Hoffmann, E., G. Neumann, et al. (2000). "A DNA transfection system for generation of influenza A virus from eight plasmids."*Proceedings of the National Academy of Sciences of the United States of America* 97(11): 6108-6113.

Hoffmann, E., S. Krauss, D. Perez, R. Webby, and R. G. Webster. (2002). "Eight-plasmid system for rapid generation of influenza virus vaccines". *Vaccine* 20:3165-3170.

Huang, I. C., W. Li, et al. (2008). "Influenza A virus neuraminidase limits viral superinfection."*Journal of virology* 82(10): 4834-4843.

Hultberg, A., N. J. Temperton, et al. (2011). "Llama-derived single domain antibodies to build multivalent, superpotent and broadened neutralizing anti-viral molecules."*PLoS One* 6(4): e17665.

Hung, I. F. N, To, K. K. W. et al. (2011). "Convalescent plasma treatment reduced mortality in patients with severe pandemic influenza A (H1N1° 2009 virus infection. CID 52: 447-456.

Ibanez, L. I., M. De Filette, et al. (2011). "Nanobodies with in vitro neutralizing activity protect mice against H5N1 influenza virus infection."*J Infect Dis* 203(8): 1063-1072.

Ilyushina, N. A., N. V. Bovin, et al. (2012). "Decreased neuraminidase activity is important for the adaptation of H5N1 influenza virus to human airway epithelium."*Journal of virology* 86(9): 4724-4733.

Ilyushina, N. A., M. F. Ducatez, et al. (2010). "Does pandemic A/H1N1 virus have the potential to become more pathogenic?"*mBio* 1(5).

Imai, M., T. Watanabe, et al. (2012). "Experimental adaptation of an influenza H5 HA confers respiratory droplet transmission to a reassortant H5 HA/H1N1 virus in ferrets."*Nature* 486(7403): 420-428.

Johansson, B. E. and E. D. Kilbourne (1993). "Dissociation of influenza virus hemagglutinin and neuraminidase eliminates their intravirionic antigenic competition."*Journal of virology* 67(10): 5721-5723.

Johansson, B. E., J. T. Matthews, et al. (1998). "Supplementation of conventional influenza A vaccine with purified viral neuraminidase results in a balanced and broadened immune response."*Vaccine* 16(9-10): 1009-1015.

Johansson, B. E., T. M. Moran, et al. (1987). "Immunologic response to influenza virus neuraminidase is influenced by prior experience with the associated viral hemagglutinin. II. Sequential infection of mice simulates human experience."*Journal of immunology* 139(6): 2010-2014.

Kang, A. S., T. M. Jones, et al. (1991). "Antibody redesign by chain shuffling from random combinatorial immunoglobulin libraries."*Proceedings of the National Academy of Sciences of the United States of America* 88(24): 11120-11123.

Kilbourne, E. D., B. A. Pokorny, et al. (2004). "Protection of mice with recombinant influenza virus neuraminidase."*The Journal of infectious diseases* 189(3): 459-461.

Lauwereys, M., M. Arbadi Ghahroudi, et al. (1998). Potent enzyme inhibitors derived from dromedary heavy-chain antibodies. *EMBO J.* 17: 3512-3520.

Li, S., J. Schulman, et al. (1993). "Glycosylation of neuraminidase determines the neurovirulence of influenza A/WSN/33 virus."*Journal of virology* 67(11): 6667-6673.

Matrosovich, M., T. Matrosovich, et al. (2006). "New low-viscosity overlay medium for viral plaque assays."*Virology journal* 3: 63.

Matrosovich, M. N., T. Y. Matrosovich, et al. (2004). "Neuraminidase is important for the initiation of influenza virus infection in human airway epithelium."*Journal of virology* 78(22): 12665-12667.

Matsuoka, Y., D. E. Swayne, et al. (2009). "Neuraminidase stalk length and additional glycosylation of the hemagglutinin influence the virulence of influenza H5N1 viruses for mice."*Journal of virology* 83(9): 4704-4708.

Mitnaul, L. J., M. N. Matrosovich, et al. (2000). "Balanced hemagglutinin and neuraminidase activities are critical for efficient replication of influenza A virus."*Journal of virology* 74(13): 6015-6020.

Nedyalkova, M. S., F. G. Hayden, et al. (2002). "Accumulation of defective neuraminidase (NA) genes by influenza A viruses in the presence of NA inhibitors as a marker of reduced dependence on NA."*The Journal of infectious diseases* 185(5): 591-598.

Nguyen, V. K., S. Muyldermans, et al. (1998). "The specific variable domain of camel heavy-chain antibodies is encoded in the germline."*J Mol Biol* 275(3): 413-418.

Rameix-Welti, M. A., M. L. Zarantonelli, et al. (2009). "Influenza A virus neuraminidase enhances meningococcal adhesion to epithelial cells through interaction with sialic acid-containing meningococcal capsules."*Infection and immunity* 77(9): 3588-3595.

Reed, H and L. Muench. (1938). "A simple method for estimating fifty percent endpoints."*American Journal of Medical Hygiene* 27:493-497.

Schepens, B., L. I. Ibanez, et al. (2011). Nanobodies specific for Respiratory Syncytial Virus Fusion protein protect against infection by inhibition of fusion. *J Inf Dis.* 204 (11):1692-701.

Schotsaert, M., T. Ysenbaert, K. Neyt, L. I. Ibanez, P. Bogaert, B. Schepens, B. N. Lambrecht, W. Fiers, and X. Saelens. (2013). "Natural and long-lasting cellular immune responses against influenza in the M2e-immune host". *Mucosal immunology* 6:276-287.

Shoji, Y., J. A. Chichester, et al. (2011). "An influenza N1 neuraminidase-specific monoclonal antibody with broad neuraminidase inhibition activity against H5N1 HPAI viruses."*Human vaccines* 7 Suppl: 199-204.

Tran, T. H., T. L. Nguyen, et al. (2004). "Avian influenza A (H5N1) in 10 patients in Vietnam."*The New England journal of medicine* 350(12): 1179-1188.

Van Borm, S., I. Thomas, et al. (2005). "Highly pathogenic H5N1 influenza virus in smuggled Thai eagles, Belgium."*Emerging infectious diseases* 11(5): 702-705.

Van Droogenbroeck, B., J. Cao, et al. (2007). "Aberrant localization and underglycosylation of highly accumulating single-chain Fv-Fc antibodies in transgenic *Arabidopsis* seeds."*Proceedings of the National Academy of Sciences of the United States of America* 104(4): 1430-1435.

Wang, M. Z., C. Y. Tai, et al. (2002). "Mechanism by which mutations at his274 alter sensitivity of influenza a virus n1 neuraminidase to oseltamivir carboxylate and zanamivir."*Antimicrob Agents Chemother* 46(12): 3809-3816.

Wong, H. K., Lee, C. K. et al. (2010). "Practical limitations of convalescent plasma collection: a case scenario in pandemic preparation for influenza A (H1N1) infection. Transfusion 50: 1967-1971.

Yamada, S., Y. Suzuki, et al. (2006). "Haemagglutinin mutations responsible for the binding of H5N1 influenza A viruses to human-type receptors."*Nature* 444(7117): 378-382.

Zhou, B., N. Zhong, et al. (2007). "Treatment with convalescent plasma for influenza A (H5N1) infection."*N Engl J Med* 357(14): 1450-1451.

The invention claimed is:

1. A VHH that specifically binds influenza neuraminidase, comprising a CDR1 loop sequence of SEQ ID NO: 1, a CDR2 loop sequence of SEQ ID NO: 3, and a CDR3 loop sequence of SEQ ID NO: 5.

2. An influenza neuraminidase binding construct comprising a VHH according to claim 1.

3. The neuraminidase binding construct according to claim 2, wherein said construct is bivalent.

4. The neuraminidase binding construct according to claim 3, wherein said VHH is fused to an Fc tail.

5. The neuraminidase binding construct according to claim 3, wherein said VHHs are linked by an IgG2c hinge.

6. The neuraminidase binding construct according to claim 2, wherein said construct comprises a sequence selected from the group consisting of SEQ ID NO: 7 and SEQ ID NO: 9.

7. A pharmaceutical composition comprising an influenza binding construct according to claim 2.

8. A pharmaceutical composition comprising an influenza binding construct according to claim 3.

9. A pharmaceutical composition comprising an influenza binding construct according to claim 6.

10. A VHH that specifically binds influenza neuraminidase, comprising a CDR1 loop sequence SEQ ID NO: 2, a CDR2 loop sequence of SEQ ID NO: 4 and a CDR3 loop sequence of SEQ ID NO: 6.

11. An influenza neuraminidase binding construct comprising a VHH according to claim 10.

12. The neuraminidase binding construct according to claim 11, wherein said construct is bivalent.

13. The neuraminidase binding construct according to claim 12, wherein said VHH is fused to an Fc tail.

14. The neuraminidase binding construct according to claim 12, wherein said VHHs are linked by an IgG2c hinge.

15. The neuraminidase binding construct according to claim 11, wherein said construct comprises a sequence selected from the group consisting of SEQ ID NO: 8 and SEQ ID NO: 10.

16. A pharmaceutical composition comprising an influenza binding construct according to claim 11.

17. A pharmaceutical composition comprising an influenza binding construct according to claim 12.

18. A pharmaceutical composition comprising an influenza binding construct according to claim 13.

* * * * *